(12) United States Patent
Schischka et al.

(10) Patent No.: US 7,915,394 B2
(45) Date of Patent: Mar. 29, 2011

(54) ALLELES OF THE OPCA GENE FROM CORYNEFORM BACTERIA

(75) Inventors: Natalie Schischka, Bielefeld (DE); Brigitte Bathe, Salzkotten (DE); Georg Thierbach, Bielefeld (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 12/696,449

(22) Filed: Jan. 29, 2010

(65) Prior Publication Data

US 2010/0196959 A1 Aug. 5, 2010

Related U.S. Application Data

(62) Division of application No. 11/383,253, filed on May 15, 2006, now Pat. No. 7,700,313.

(60) Provisional application No. 60/710,314, filed on Aug. 22, 2005.

(30) Foreign Application Priority Data

May 24, 2005 (DE) .......................... 10 2005 023 829

(51) Int. Cl.
*C12P 1/00* (2006.01)
*C12P 13/04* (2006.01)
*C07H 21/02* (2006.01)
*C07H 21/04* (2006.01)
*C12N 15/63* (2006.01)
*C12N 1/20* (2006.01)
*C12N 1/21* (2006.01)

(52) U.S. Cl. ...... 536/23.1; 435/41; 435/106; 435/320.1; 435/252.1; 435/252.3

(58) Field of Classification Search ........................ None
See application file for complete search history.

(56) References Cited

U.S. PATENT DOCUMENTS

2002/0048793 A1   4/2002   Bathe et al. .................. 435/69.1
2003/0219881 A1   11/2003  Brigitte et al. ................ 435/106

FOREIGN PATENT DOCUMENTS

EP    1 669 369      6/2006
WO    WO 01/04322    1/2001
WO    WO2004/054381  7/2004

OTHER PUBLICATIONS

European Search Report (Forms PCT/ISA/220,PCT/ISA/210 and PCT/ISA/237), 2006.
Database UniProt, Mar. 1, 2003, "Putative oxppcycle protein OpcA", XP002414959 gefunden im EBI Database accession No. Q8FT73, Zusammenfassung.
Database UniProt, Jul. 5, 2004, "Hypothetical protein", XP002414960 gefunden im EBI Database accession No. Q6NH40, Zusammenfassung.
Branden et al., "Introduction to Protein Structure Second Edition", Garland Publishing Inc., New York, 1999.
Witkowski et al., Biochemistry, 38, 11643-11650, 1999.
Wishart et al., Journal of Biological Chemistry, vol. 270, No. 45, pp. 26782-26785, 1995.
Kisselev, Structure, vol. 10, pp: 8-9, 2002.
Nishio et al. (Comparative Complete Genome Sequence Analysis of the Amino Acid Replacements Responsible for the Thermostability of Corynebacterium efficiens, Genome Res. 2003 13: 1572-1579).
NCBI search result of "corynebacterium", Retrieved from the Internet <URL: http://www.ncbi.nlm.nih.gov/Taxonomy/Browser/wwwtax.cgi?id=1716>, Retrieved on Jun. 3, 2009.
European Search Report (Forms PCT/ISA/220, PCT/ISA/210 and PCT/ISA/237) dated Feb. 9, 2007.

*Primary Examiner* — Suzanne M Noakes
*Assistant Examiner* — Jae W Lee
(74) *Attorney, Agent, or Firm* — Smith, Gambrell, Russell, LLP

(57) ABSTRACT

The invention relates to mutants and alleles of the opcA gene of coryneform bacteria, which encode variants of the OpcA subunit of glucose 6-phosphate dehydrogenase (EC: 1.1.1.49), and to processes for preparing amino acids, in particular L-lysine and L-tryptophan, by using bacteria which harbor said alleles.

43 Claims, No Drawings

US 7,915,394 B2

ALLELES OF THE OPCA GENE FROM CORYNEFORM BACTERIA

CROSS REFERENCE TO RELATED APPLICATIONS

This application is a division of U.S. patent application Ser. No. 11/383,253, filed 15 May 2006, now U.S. Pat. No. 7,700,313, and claims the benefit of priority to U.S. Patent Application Ser. No. 60/710,314, filed 22 Aug. 2005, and German Patent Application Serial No. 102005023829.7, filed 24 May 2005, all of which are herein incorporated by reference in their entirety.

BACKGROUND OF THE INVENTION

1. Field of the Invention

The invention relates to mutants and alleles of the opcA gene which encode variants of the OpcA subunit of glucose 6-phosphate dehydrogenase (EC: 1.1.1.49) and to processes for preparing amino acids, in particular L-lysine and L-tryptophan, by using bacteria which harbor said alleles.

2. Prior Art

Amino acids are applied in human medicine, in the pharmaceutical industry, in the food industry and especially in animal nutrition.

Amino acids are known to be prepared by fermentation of strains of coryneform bacteria, in particular *Corynebacterium glutamicum*. Due to the great importance, continuous efforts are made to improve the production processes. Said processes may be improved with respect to fermentation-related measures such as, for example, stirring and oxygen supply or the composition of the nutrient media, such as, for example, sugar concentration during the fermentation, or the working-up into product form, for example by means of ion exchange chromatography, or the intrinsic performance characteristics of the microorganism itself.

The performance characteristics of said microorganisms are improved by applying methods of mutagenesis, selection and mutant choice. This enables strains to be obtained which are resistant to antimetabolites or auxotrophic for metabolites which are of regulatory importance, and produce amino acids. A known antimetabolite is the lysine analog S-(2-aminoethyl)-L-cysteine (AEC).

For some years now, methods of recombinant DNA technology have likewise been employed in order to improve L-amino acid-producing *Corynebacterium* strains, by amplifying individual amino acid biosynthesis genes and studying the effect on amino acid production. A summary on a wide variety of aspects of the genetics, the metabolism and the biotechnology of *Corynebacterium glutamicum* can be found in Pühler (chief ed.) in Journal of Biotechnology 104 (1-3), 1-338, 2003.

Moritz et al. (European Journal of Biochemistry 267, 3442-3452 (2000)) report physiological and biochemical studies on glucose 6-phosphate dehydrogenase of *Corynebacterium glutamicum*. According to studies by Moritz et al., glucose 6-phosphate hydrogenase consists of a Zwf subunit and an OpcA subunit.

Moritz et al. (European Journal of Biochemistry 267, 3442-3452 (2000) describe a method of determining the enzymic activity of glucose 6-phosphate dehydrogenase.

The nucleotide sequence of the gene encoding the OpcA subunit of *Corynebacterium glutamicum* glucose 6-phosphate dehydrogenase is generally accessible, inter alia, in the database of the National Center for Biotechnology Information (NCBI, Bethesda, Md., USA) of the National Library of Medicine (Bethesda, Md., USA), under the number AX121828. It can furthermore be found as sequence No. 1744 in the patent application EP 1108790.

Other databases such as, for example, the nucleotide sequence database of the European Molecular Biologies Laboratories (EMBL, Heidelberg, Germany and Cambridge, UK) or that of the Swiss Institute of Bioinformatics (Swissprot, Geneva, Switzerland) or that of the Protein Information Resource Database (PIR, Washington, D.C., USA) may likewise be utilized.

The microbial biosynthesis of L-amino acids in coryneform bacteria is a complex system and linked on multiple levels to various other metabolic pathways in the cell. It is therefore not possible to predict whether mutation alters the OpcA polypeptide of glucose 6-phosphate dehydrogenase in such a way that production of L-amino acids is improved. For reasons of better clarity, SEQ ID NO: 1 depicts the nucleotide sequence of the zwf gene encoding the OpcA subunit of *Corynebacterium glutamicum* glucose 6-phosphate dehydrogenase ("wild type gene"), according to the information of the NCBI database, and SEQ ID NO: 2 and 4 depict the amino acid sequence resulting therefrom of the encoded glucose 6-phosphate dehydrogenase. In addition, SEQ ID NO: 3 indicates nucleotide sequences located upstream and downstream.

OBJECT OF THE INVENTION

The inventors have set themselves the object of providing improved strains of microorganisms which produce increased amounts of amino acids, in particular L-lysine and L-tryptophan.

DESCRIPTION OF THE INVENTION

The invention relates to mutants of coryneform bacteria, which have been generated in vitro and/or in vivo or have been isolated, which preferably secrete amino acids and which comprise a gene or allele which encodes the OpcA subunit of glucose 6-phosphate dehydrogenase and wherein the amino acid sequence of said polypeptide comprises individual or a combination of amino acids selected from the group consisting of a) any proteinogenic amino acid other than L-tyrosine in position 107 of said amino acid sequence,
b) any proteinogenic amino acid other than L-lysine in position 219 of said amino acid sequence,
c) any proteinogenic amino acid other than L-proline in position 233 of said amino acid sequence, and
d) any proteinogenic amino acid other than L-tyrosine in position 261 of said amino acid sequence.

Preference is given to the amino acid L-histidine being in position 107 of said amino acid sequence, to the amino acid L-asparagine being in position 219, to the amino acid L-serine being in position 233 and to the amino acid L-histidine being in position 261.

The polypeptide which is present in the mutants of the invention may likewise be referred to as OpcA polypeptide, OpcA polypeptide of glucose 6-phosphate dehydrogenase, as OpcA subunit of glucose 6-phosphate dehydrogenase, or as OpcA polypeptide subunit. EP 1 108 790 (see SEQ ID NO: 1744 in Table 1) refers to the OpcA polypeptide also as "glucose 6-phosphate dehydrogenase assembly protein".

Among the coryneform bacteria, preference is given to the genus *Corynebacterium*. Particular preference is given to amino acid-secreting strains which are based on the following species:

*Corynebacterium efficiens*, for example the strain DSM44549,
*Corynebacterium glutamicum*, for example the strain ATCC13032,
*Corynebacterium thermoaminogenes* for example the strain FERM BP-1539, and
*Corynebacterium ammoniagenes*, for example the strain ATCC6871, very particular preference being given to the species *Corynebacterium glutamicum*.

Some representatives of the species *Corynebacterium glutamicum* are also known under different species names in the prior art. These include, for example:
*Corynebacterium acetoacidophilum* ATCC13870,
*Corynebacterium lilium* DSM20137,
*Corynebacterium melassecola* ATCC 17965,
*Brevibacterium flavum* ATCC 14067,
*Brevibacterium lactofermentum* ATCC13869, and
*Brevibacterium divaricatum* ATCC 14020.

Examples of known representatives of amino acid-secreting strains of coryneform bacteria are
the L-lysine-producing strains
*Corynebacterium glutamicum* DM58-1/pDM6 (=DSM4697) described in EP 0 358 940,
*Corynebacterium glutamicum* MH20-22B (=DSM16835) described in Menkel et al. (Applied and Environmental Microbiology 55(3), 684-688 (1989)),
*Corynebacterium glutamicum* AHP-3 (=FermBP-7382) described in EP 1 108 790,
*Corynebacterium thermoaminogenes* AJ12521 (=FERM BP-3304) described in U.S. Pat. No. 5,250,423,
or the L-tryptophan-producing strains
*Corynebacterium glutamicum* K76 (=FermBP-1847) described in U.S. Pat. No. 5,563,052,
*Corynebacterium glutamicum* BPS13 (=FermBP-1777) described in U.S. Pat. No. 5,605,818, and
*Corynebacterium glutamicum* FermBP-3055 described in U.S. Pat. No. 5,235,940.

Information on the taxonomic classification of strains of this group of bacteria can be found, inter alia, in Seiler (Journal of General Microbiology 129, 1433-1477 (1983)), Kämpfer and Kroppenstedt (Canadian Journal of Microbiology 42, 989-1005 (1996)), Liebl et al. (International Journal of Systematic Bacteriology 41, 255-260 (1991)) and in U.S. Pat. No. 5,250,434.

Strains denoted "ATCC" may be obtained from the American Type Culture Collection (Manassas, Va., USA). Strains denoted "DSM" may be obtained from the Deutsche Sammlung von Mikroorganismen and Zellkulturen (DSMZ, Brunswick, Germany). Strains denoted "FERM" may be obtained from the National Institute of Advanced Industrial Science and Technology (AIST Tsukuba Central 6, 1-1-1 Higashi, Tsukuba Ibaraki, Japan). The *Corynebacterium thermoaminogenes* strains mentioned (FERM BP-1539, FERM BP-1540, FERM BP-1541 and FERM BP-1542) are described in U.S. Pat. No. 5,250,434.

The term proteinogenic amino acids means the amino acids occurring in natural proteins, i.e. in proteins of microorganisms, plants, animals and humans. These include in particular L-amino acids selected from the group consisting of L-aspartic acid, L-asparagine, L-threonine, L-serine, L-glutamic acid, L-glutamine, glycine, L-alanine, L-cysteine, L-valine, L-methionine, L-isoleucine, L-leucine, L-tyrosine, L-phenylalanine, L-histidine, L-lysine, L-tryptophan, L-proline and L-arginine.

The mutants of the invention preferably secrete said proteinogenic amino acids, in particular L-lysine and L-tryptophan. The term amino acids also comprises their salts such as, for example, lysine monohydrochloride or lysine sulfate in the case of the amino acid L-lysine.

The invention furthermore relates to mutants of coryneform bacteria, which comprise an opcA allele encoding an OpcA polypeptide which comprises the amino acid sequence of SEQ ID NO: 2, which sequence comprises one or more of the amino acid substitutions selected from the group consisting of:
a) L-tyrosine in position 107 is substituted with a different proteinogenic amino acid, preferably L-histidine,
b) L-lysine in position 219 is substituted with a different proteinogenic amino acid, preferably L-asparagine,
c) L-proline in position 233 is substituted with a different proteinogenic amino acid, preferably L-serine, and
d) L-tyrosine in position 261 is substituted with a different proteinogenic amino acid, preferably L-histidine.

The invention furthermore relates to mutants of coryneform bacteria, which comprise an opcA allele encoding an OpcA polypeptide, wherein the amino acid sequence of said polypeptide has one or more of the amino acids selected from the group consisting of:
a) any proteinogenic amino acid other than L-tyrosine, preferably L-histidine, in position 107 of said amino acid sequence,
b) any proteinogenic amino acid other than L-lysine, preferably L-asparagine, in position 219 of said amino acid sequence,
c) any proteinogenic amino acid other than L-proline, preferably L-serine, in position 233 of said amino acid sequence, and
d) any proteinogenic amino acid other than L-tyrosine, preferably L-histidine, in position 261 of said amino acid sequence, with the allele comprising a nucleotide sequence identical to the nucleotide sequence of a polynucleotide which is obtainable by a polymerase chain reaction (PCR) using a primer pair whose nucleotide sequences comprise in each case at least 15 contiguous nucleotides selected from the nucleotide sequence between positions 1 and 334 of SEQ ID NO: 3 and from the complementary nucleotide sequence between positions 1600 and 1292 of SEQ ID NO: 3. An example of a primer pair of this kind is the primer pair opcA-A1 and opcA-E1 depicted in SEQ ID NO: 11 and SEQ ID NO: 12. The preferred starting material (template DNA) is chromosomal DNA of coryneform bacteria which have been treated in particular with a mutagen. Particular preference is given to the chromosomal DNA of the genus *Corynebacterium* and very particular preference is given to that of the species *Corynebacterium glutamicum*.

The invention furthermore relates to mutants of coryneform bacteria, which comprise an opcA allele encoding an OpcA polypeptide which comprises an amino acid sequence having a length corresponding to 319 L-amino acids, said amino acid sequence of said polypeptide having one or more of the amino acids selected from the group consisting of:
a) any proteinogenic amino acid other than L-tyrosine, preferably L-histidine, in position 107 of said amino acid sequence,
b) any proteinogenic amino acid other than L-lysine, preferably L-asparagine, in position 219 of said amino acid sequence,
c) any proteinogenic amino acid other than L-proline, preferably L-serine, in position 233 of said amino acid sequence, and d) any proteinogenic amino acid other than L-tyrosine, preferably L-histidine, in position 261 of said amino acid sequence.

The invention furthermore relates to mutants of coryneform bacteria, which comprise an opcA allele an OpcA polypeptide which comprises, in positions 107 to 261 of the amino acid sequence, the amino acid sequence corresponding to positions 107 to 261 of SEQ ID NO: 6. Preferably, the amino acid sequence of the encoded polypeptide comprises an amino acid sequence corresponding to positions 98 to 270 of SEQ ID NO: 6 or to positions 83 to 285 of SEQ ID NO: 6 or to positions 63 to 305 of SEQ ID NO: 6 or to positions 38 to 315 of SEQ ID NO: 6 or to positions 8 to 315 of SEQ ID NO: 6 or to positions 2 to 315 of SEQ ID NO: 6 or to positions 2 to 317 of SEQ ID NO: 6 or to positions 2 to 319 of SEQ ID NO: 6. Very particular preference is given to the length of the encoded polypeptide comprising 319 amino acids.

The invention furthermore relates to mutants of coryneform bacteria, which comprise an opcA allele encoding an OpcA polypeptide, said amino acid sequence of said polypeptide having one or more of the amino acids selected from the group consisting of:
  a) any proteinogenic amino acid other than L-tyrosine, preferably L-histidine, in position 107 of said amino acid sequence,
  b) any proteinogenic amino acid other than L-lysine, preferably L-asparagine, in position 219 of said amino acid sequence,
  c) any proteinogenic amino acid other than L-proline, preferably L-serine, in position 233 of said amino acid sequence, and
  d) any proteinogenic amino acid other than L-tyrosine, preferably L-histidine, in position 261 of said amino acid sequence,
and whose amino acid sequence is moreover at least 90%, preferably at least 92% or at least 94% or at least 96%, and very particularly preferably at least 97% or at least 98% or at least 99% or 100%, identical to the amino acid sequences of SEQ ID NO: 6 or 2.

The invention furthermore relates to mutants of coryneform bacteria, which comprise an opcA allele encoding an OpcA polypeptide, said amino acid sequence of said polypeptide having one or more of the amino acids selected from the group consisting of:
  a) any proteinogenic amino acid other than L-tyrosine, preferably L-histidine, in position 107 of said amino acid sequence,
  b) any proteinogenic amino acid other than L-lysine, preferably L-asparagine, in position 219 of said amino acid sequence,
  c) any proteinogenic amino acid other than L-proline, preferably L-serine, in position 233 of said amino acid sequence, and
  d) any proteinogenic amino acid other than L-tyrosine, preferably L-histidine, in position 261 of said amino acid sequence,
and whose nucleotide sequence is moreover at least 90%, preferably at least 92% or at least 94% or at least 96%, and very particularly preferably at least 97% or at least 98% or at least 99% or 100%, identical to the nucleotide sequence of SEQ ID NO:5 or 1.

An example of a nucleotide sequence of an opcA allele, which possesses at least 99% identity to the nucleotide sequence of SEQ ID NO: 5, is depicted in SEQ ID NO: 7. In addition to the nucleotide substitutions of thymine with cytosine in position 319, of adenine with cytosine in position 657, of cytosine with thymine in position 697 and of thymine with cytosine in position 781 (see SEQ ID NO: 5), the nucleotide sequence of this opcA allele has the nucleotide substitutions of cytosine with thymine in position 402, of thymine with cytosine in position 600 and of guanine with cytosine in position 648 (see SEQ ID NO: 7). The phrase "guanine with cytosine in position 648"—and comparable phrases—means that the nucleobase guanine present in position 648 of the wild type sequence of the coding region (see SEQ ID NO: 1) has been replaced with cytosine (see SEQ ID NO: 7).

Conservative amino acid substitutions are known to alter the enzyme activity only insignificantly. Accordingly, the opcA allele which is present in the mutants of the invention and which encodes an OpcA polypeptide comprising one or more of the amino acid substitutions of the invention may comprise one (1) or more conservative amino acid substitution(s), in addition to the amino acid sequence depicted in SEQ ID NO: 6. Preference is given to the polypeptide comprising no more than two (2), no more than three (3), no more than four (4) or no more than five (5), conservative amino acid substitutions.

In the case of the aromatic amino acids, the substitutions are said to be conservative when phenylalanine, tryptophan and tyrosine are substituted for one another. In the case of the hydrophobic amino acids, the substitutions are said to be conservative when leucine, isoleucine and valine are substituted for one another. In the case of the polar amino acids, the substitutions are said to be conservative when glutamine and asparagine are substituted for one another. In the case of the basic amino acids, the substitutions are said to be conservative when arginine, lysine and histidine are substituted for one another. In the case of the acidic amino acids, the substitutions are said to be conservative when aspartic acid and glutamic acid are substituted for one another. In the case of the hydroxyl group-containing amino acids, the substitutions are said to be conservative when serine and threonine are substituted for one another.

Finally, the invention relates to mutants of coryneform bacteria, which comprise an opcA allele encoding an OpcA polypeptide which comprises the amino acid sequence of SEQ ID NO: 6.

Enzymes intrinsic to the host, called amino peptidases, are known to remove the terminal methionine during protein synthesis.

The invention also relates to opcA alleles which encode OpcA polypeptides of the invention, depicted by way of example as SEQ ID NO: 6, and which comprise one or more insertion(s) or deletion(s). The polypeptide preferably comprises no more than 5, no more than 4, no more than 3 or no more than 2 amino acid insertions or deletions.

Insertions and deletions or conservative amino acid substitutions of this kind essentially do not affect the enzymic activity of the glucose 6-phosphate dehydrogenases comprising the corresponding OpcA subunit. "Essentially do not affect" means that the enzymic activity of the variants mentioned differs by no more than 10%, no more than 7.5%, no more than 5%, no more than 2.5% or no more than 1% from the activity of a glucose 6-phosphate dehydrogenase comprising an OpcA polypeptide subunit with the amino acid sequence of SEQ ID NO: 2, said sequence comprising one or more of the amino acid substitutions selected from the group consisting of
  a) L-histidine instead of L-tyrosine in position 107
  b) L-asparagine instead of L-lysine in position 219
  c) L-Serine instead of L-proline in position 233, and
  d) L-histidine instead of L-tyrosin in position 261.

The mutants of the invention may be prepared by classical in-vivo mutagenesis methods with cell populations of coryneform bacteria by using mutagenic substances such as, for example, N-methyl-N'-nitro-N-nitrosoguanidine (MNNG), ethyl methanesulfonate (EMS), 5-bromouracil, or ultraviolet light. Mutagenesis methods are described, for example, in Manual of Methods for General Bacteriology (Gerhard et al. (Eds.), American Society for Microbiology, Washington, D.C., USA, 1981) or in Tosaka et al. (Agricultural and Biological Chemistry 42(4), 745-752 (1978)) or in Konicek et al. (Folia Microbiologica 33, 337-343 (1988)). Typical mutageneses using MNNG comprise concentrations of from 50 to 500 mg/l or else higher concentrations of up to a maximum of 1 g/l, an incubation time of from 1 to 30 minutes at a pH of from 5.5 to 7.5. Under these conditions, the number of viable cells is reduced by a proportion of from approx. 50% to 90% or approx. 50% to 99% or approx. 50% to 99.9% or more.

Mutants or cells are removed from the mutagenized cell population and propagated. Preference is given to investigating, in a further step, their ability to secrete amino acids, preferably L-lysine or L-tryptophan, in a batch culture using a suitable nutrient medium. Suitable nutrient media and assay conditions are described, inter alia, in U.S. Pat. No. 6,221, 636, in U.S. Pat. No. 5,840,551, in U.S. Pat. No. 5,770,409, in U.S. Pat. No. 5,605,818, in U.S. Pat. No. 5,275,940 and in U.S. Pat. No. 4,224,409. In this way, mutants are identified which, compared to the parent strain or non-mutagenized starting strain, secrete an increased amount of amino acids into the nutrient medium or the cell interior. These include, for example, those mutants whose amino acid secretion has increased by at least 0.5%.

Subsequently, DNA of the mutants is provided or isolated from the latter, and the corresponding polynucleotide is synthesized with the aid of the polymerase chain reaction using primer pairs which allow amplification of the opcA gene or of the opcA alleles of the invention or of the mutations of the invention in positions 107, 219, 233 and 261 of the amino acid sequence of the OpcA polypeptide. Preference is given to isolating the DNA from those mutants which, in comparison with the starting strain, secrete, or accumulate in the cell interior, an increased amount of amino acids.

To this end, it is possible to select any primer pairs from the nucleotide sequence located upstream and downstream of the mutation of the invention and from the nucleotide sequence complementary thereto. A primer of a primer pair here preferably comprises at least 15, at least 18, at least 20, at least 21 or at least 24, contiguous nucleotides selected from the nucleotide sequence between positions 1 and 652 of SEQ ID NO: 3. The corresponding second primer of a primer pair comprises at least 15, at least 18, at least 20, at least 21 or at least 24, contiguous nucleotides selected from the complementary nucleotide sequence of positions 1600 and 1118 of SEQ ID NO: 3. If it is desired to amplify the coding region, then the primer pair is preferably selected from the nucleotide sequence between positions 1 and 334 of SEQ ID NO: 3 and from the complementary nucleotide sequence between positions 1600 and 1292 of SEQ ID NO: 3. If it is desired to amplify part of the coding region, as indicated, for example, in SEQ ID NO: 15 and 17, then the primer pair is preferably selected from the nucleotide sequence between positions 335 and 652 of SEQ ID NO: 3 and from the complementary nucleotide sequence between positions 1291 and 1118 of SEQ ID NO: 3.

Examples of suitable primer pairs are the opcA-A1 and opcA-E1 primer pair depicted under SEQ ID NO: 11 and SEQ ID NO: 12 and the opcA-int1 and opcA-int2 primer pair depicted under SEQ ID NO: 13 and SEQ ID NO: 14. In addition, the primer may be provided with recognition sites for restriction enzymes, with a biotin group or further accessories as described in the prior art. The total length of the primer is usually no more than 30, 40, 50 or 60 nucleotides.

Usually, thermostable DNA polymerases are employed in the preparation of polynucleotides by amplification of selected sequences such as the opcA allele of the invention from initially introduced DNA, for example chromosomal DNA (template DNA), via amplification by means of PCR. Examples of DNA polymerases of this kind are Taq polymerase of *Thermus aquaticus*, which is sold, inter alia, by Qiagen (Hilden, Germany), Vent polymerase of *Thermococcus litoralis*, sold, inter alia, by New England Biolabs (Frankfurt, Germany), or Pfu polymerase of *Pyrococcus furiosus*, sold, inter alia, by Stratagene (La Jolla, USA). Preference is given to polymerases having proof-reading activity. Proofreading activity means that these polymerases are capable of recognizing wrongly incorporated nucleotides and rectifying the error by renewed polymerization (Lottspeich and Zorbas, Bioanalytik, Spektrum Akademischer Verlag, Heidelberg, Germany (1998)). Examples of polymerases having proofreading activity are Vent polymerase and Pfu polymerase.

The conditions in the reaction mixture are set according to the information provided by the manufacturer. The polymerases are usually supplied by the manufacturer together with the customary buffer which usually has concentrations of 10-100 mM Tris/HCl and 6-55 mM KCl at pH 7.5-9.3. Magnesium chloride is added in a concentration of 0.5-10 mM, if not present in the buffer supplied by the manufacturer. Furthermore, deoxynucleoside triphosphates are added in a concentration of 0.1-16.6 mM to the reaction mixture. The primers, in a final concentration of 0.1-3 µM, and template DNA, in the optimal case from $10^2$ to $10^5$ copies, are initially introduced into the reaction mixture. An amount of 2-5 units of the appropriate polymerase is added to the reaction mixture. A typical reaction mixture has a volume of 20-100 µl.

Further additives which may be added to the reaction are bovine serum albumin, Tween-20, gelatin, glycerol, formamide or DMSO (Dieffenbach and Dveksler, PCR Primer A Laboratory Manual, Cold Spring Harbor Laboratory Press, USA 1995).

A typical PCR profile consists of three different, successively repeated temperature stages. Initially, the reaction is started by increasing the temperature to 92° C.-98° C. for 4 to 10 minutes in order to denature the initially introduced DNA. This is followed repeatedly by first a step of denaturing the initially introduced DNA at approximately 92-98° C. for 10-60 seconds, then a step of 10-60 seconds of binding the primers to the initially introduced DNA at a particular temperature dependent on said primers (annealing temperature), which from experience is from 50° C. to 60° C. and can be calculated for each primer pair individually. Detailed information on this can be found by the skilled worker in Rychlik et al. (Nucleic Acids Research 18 (21): 6409-6412). Subsequently, a synthesis step of extending the initially introduced primers (extension) at the activity optimum of the polymerase, indicated in each case and usually in the range from 73° C. to 67° C., preferably 72° C. to 68° C., depending on the polymerase. The duration of this extension step depends on the performance of the polymerase and on the length of the PCR product to be amplified. In a typical PCR, this step lasts 0.5-8 minutes, preferably 2-4 minutes. These three steps are repeated 30 to 35 times, where appropriate up to 50 times. A final "extension" step of 4-10 minutes ends the reaction. The polynucleotides prepared in this manner are also referred to as amplicons; the term nucleic acid fragment is likewise common.

Further details and information regarding PCR can be found by the skilled worker in the manual PCR-Strategies (Innis, Felfand and Sninsky, Academic Press, Inc., 1995), in PCR Primer—a laboratory manual, in the manual by Gait: Oligonucleotide synthesis: A Practical Approach (IRL Press, Oxford, UK, 1984) and in Newton and Graham: PCR (Spektrum Akademischer Verlag, Heidelberg, Germany, 1994).

The nucleotide sequence is subsequently determined, for example by the chain termination method of Sanger et al. (Proceedings of the National Academies of Sciences, U.S.A., 74, 5463-5467 (1977)) with the modifications indicated by Zimmermann et al. (Nucleic Acids Research 18, 1067 pp (1990)), and the polypeptide encoded by said nucleotide sequence is analyzed, in particular with respect to the amino acid sequence. For this purpose, the nucleotide sequence is entered into a program for translating DNA sequence into an amino acid sequence. Examples of suitable programs are the program "Patentin" which is available from patent offices, for example the US Patent and Trademark Office (USPTO), or "Translate Tool" which is available on the ExPASy Proteomics Server on the World Wide Web (Gasteiger et al., Nucleic Acids Research 31, 3784-3788 (2003)).

In this way, mutants are identified whose opcA alleles encode OpcA polypeptides which comprise the mutations of the invention.

Accordingly, the invention relates to a mutant of a coryneform bacterium, which is obtainable by the following steps:
a) treating a coryneform bacterium capable of secreting amino acids with a mutagenic agent,
b) isolating and propagating the mutant generated in a),
c) preferably determining the ability of said mutant to secrete in a medium or to accumulate in the cell interior at least 0.5% more amino acid than the coryneform bacterium employed in a),
d) providing nucleic acid from the mutant obtained in b),
e) preparing a nucleic acid molecule/amplicon/nucleic acid fragment, using the polymerase chain reaction, of the nucleic acid from d) and of a primer pair consisting of a first primer comprising at least 15 contiguous nucleotides selected from the nucleotide sequence between positions 1 and 334 of SEQ ID NO: 3 and a second primer comprising at least 15 contiguous nucleotides selected from the complementary nucleotide sequence between positions 1600 and 1292 of SEQ ID NO: 3,
f) determining the nucleotide sequence of the nucleic acid molecule obtained in e) and determining the encoded amino acid sequence,
g) comparing, where appropriate, the amino acid sequence determined in f) with SEQ ID NO:6, and
h) identifying a mutant comprising a polynucleotide which encodes a polypeptide comprising one or more of the amino acids selected from the group consisting of
   a) any proteinogenic amino acid other than L-tyrosine, preferably L-histidine, in position 107 of said amino acid sequence,
   b) any proteinogenic amino acid other than L-lysine, preferably L-asparagine, in position 219 of said amino acid sequence,
   c) any proteinogenic amino acid other than L-proline, preferably L-serine, in position 233 of said amino acid sequence, and
   d) any proteinogenic amino acid other than L-tyrosine, preferably L-histidine, in position 261 of said amino acid sequence.

The mutants generated in this way typically comprise one (1) copy of one of the opcA alleles described. The invention likewise relates to the process described here.

SEQ ID NO: 5 depicts, by way of example, the coding regions of an opcA allele of a mutant of the invention. The coding region of the wild type gene is depicted as SEQ ID NO: 1.

SEQ ID NO: 1 comprises the TAT codon, coding for the amino acid L-tyrosine, in positions 319 to 321. SEQ ID NO: 5 comprises the nucleobase cytosine in position 319. This thymine-cytosine transition results in the CAT codon, coding for the amino acid L-histidine, in positions 319 to 321.

SEQ ID NO: 1 comprises the AAA codon, coding for the amino acid L-lysine, in positions 655 to 657. SEQ ID NO: 5 comprises the nucleobase cytosine in position 657. This adenine-cytosine transversion results in the AAC codon, coding for the amino acid L-asparagine, in positions 655 to 657.

SEQ ID NO: 1 comprises the CCA codon, coding for the amino acid L-proline, in positions 697 to 699. SEQ ID NO: 5 comprises the nucleobase thymine in position 697. This cytosine-thymine transition results in the TCA codon, coding for the amino acid L-serine in positions 697 to 699.

SEQ ID NO: 1 comprises the TAT codon, coding for the amino acid L-tyrosine, in positions 781 to 783. SEQ ID NO: 5 comprises the nucleobase cytosine in position 781. This thymine-cytosine transition results in the CAT codon, coding for the amino acid L-histidine, in positions 781 to 783.

In addition, the nucleotide sequence depicted in SEQ ID NO: 5 may comprise further base substitutions which have resulted from the mutagenesis treatment but which do not manifest themselves in an altered amino acid sequence. Such mutations are referred to in the art also as silent or neutral mutations. These silent mutations may likewise already be present in the coryneform bacterium used for said mutagenesis treatment. Examples of such silent mutations are the cytosine-thymine transition in position 402, the thymine-cytosine transition in position 600 and the guanine-cytosine transversion in position 648, as depicted in SEQ ID NO: 7.

The coryneform bacteria used for the mutagenesis preferably already have the ability to secrete the desired amino acid into the surrounding nutrient medium or fermentation broth or to accumulate it in the cell interior.

L-Lysine-producing coryneform bacteria typically possess a feedback-resistant or desensibilized aspartate kinase. Feedback-resistant aspartate kinases mean aspartate kinases which, compared to the wild type, have a lower sensitivity to the inhibition by mixtures of lysine and threonine or mixtures of AEC (aminoethylcysteine) and threonine or lysine alone or AEC alone. The genes or alleles encoding these desensibilized aspartate kinases are also referred to as lysC$^{FBR}$ alleles. The prior art (Table 1) describes numerous lysC$^{FBR}$ alleles encoding aspartate kinase variants which have amino acid substitutions in comparison with the wild type protein. SEQ ID NO: 19 depicts the coding region of the wild type lysC gene of *Corynebacterium glutamicum* according to accession number AX756575 of the NCBI database, and SEQ ID NO: 20 depicts the protein encoded by said gene.

TABLE 1 lysC$^{FBR}$ alleles encoding feedback-resistant aspartate kinases

| Name of allele | Further information | Reference | Accession number |
|---|---|---|---|
| lysC$^{FBR}$ E05108 | | JP 1993184366-A (sequence 1) | E05108 |
| lysC$^{FBR}$ E06825 | lysC A279T | JP 1994062866-A (sequence 1) | E06825 |
| lysC$^{FBR}$ E06826 | lysC A279T | JP 1994062866-A (sequence 2) | E06826 |

TABLE 1-continued lysC$^{FBR}$ alleles encoding feedback-resistant aspartate kinases

| Name of allele | Further information | Reference | Accession number |
|---|---|---|---|
| lysC$^{FBR}$ E06827 | | JP 1994062866-A (sequence 3) | E06827 |
| lysC$^{FBR}$ E08177 | | JP 1994261766-A (sequence 1) | E08177 |
| lysC$^{FBR}$ E08178 | lysC A279T | JP 1994261766-A (sequence 2) | E08178 |
| lysC$^{FBR}$ E08179 | lysC A279V | JP 1994261766-A (sequence 3) | E08179 |
| lysC$^{FBR}$ E08180 | lysC S301F | JP 1994261766-A (sequence 4) | E08180 |
| lysC$^{FBR}$ E08181 | lysC T308I | JP 1994261766-A (sequence 5) | E08181 |
| lysC$^{FBR}$ E08182 | | JP 1994261766-A (sequence 6) | E08182 |
| lysC$^{FBR}$ E12770 | | JP 1997070291-A (sequence 13) | E12770 |
| lysC$^{FBR}$ E14514 | | JP 1997322774-A (sequence 9) | E14514 |
| lysC$^{FBR}$ E16352 | | JP 1998165180-A (sequence 3) | E16352 |
| lysC$^{FBR}$ E16745 | | JP 1998215883-A (sequence 3) | E16745 |
| lysC$^{FBR}$ E16746 | | JP 1998215883-A (sequence 4) | E16746 |
| lysC$^{FBR}$ I74588 | | US 5688671-A (sequence 1) | I74588 |
| lysC$^{FBR}$ I74589 | lysC A279T | US 5688671-A (sequence 2) | I74589 |
| lysC$^{FBR}$ I74590 | | US 5688671-A (sequence 7) | I74590 |
| lysC$^{FBR}$ I74591 | lysC A279T | US 5688671-A (sequence 8) | I74591 |
| lysC$^{FBR}$ I74592 | | US 5688671-A (sequence 9) | I74592 |
| lysC$^{FBR}$ I74593 | lysC A279T | US 5688671-A (sequence 10) | I74593 |
| lysC$^{FBR}$ I74594 | | US 5688671-A (sequence 11) | I74594 |
| lysC$^{FBR}$ I74595 | lysC A279T | US 5688671-A (sequence 12) | I74595 |
| lysC$^{FBR}$ I74596 | | US 5688671-A (sequence 13) | I74596 |
| lysC$^{FBR}$ I74597 | lysC A279T | US 5688671-A (sequence 14) | I74597 |
| lysC$^{FBR}$ X57226 | lysC S301Y | EP0387527 Kalinowski et al., Molecular and General Genetics 224: 317-324 (1990) | X57226 |
| lysC$^{FBR}$ L16848 | lysC G345D | Follettie and Sinskey NCBI Nucleotide Database (1990) | L16848 |
| lysC$^{FBR}$ L27125 | lysC R320G lysC G345D | Jetten et al., Applied Microbiology Biotechnology 43: 76-82 (1995) | L27125 |
| lysC$^{FBR}$ | lysC T311I | WO0063388 (sequence 17) | |
| lysC$^{FBR}$ | lysC S301F | U.S. Pat. No. 3,732,144 | |
| lysC$^{FBR}$ | lysC S381F | EP0435132 | |
| lysC$^{FBR}$ | lysC S317A | U.S. Pat. No. 5,688,671 (sequence 1) | |
| lysC$^{FBR}$ | lysC T380I | WO 01/49854 | |

L-Lysine-secreting coryneform bacteria typically possess one or more of the amino acid substitutions listed in Table 1.

Preference is given to the following lysC$^{FBR}$ alleles: lysC A279T (substitution of alanine in position 279 of the encoded aspartate kinase protein according to SEQ ID NO: 20 with threonine), lysC A279V (substitution of alanine in position 279 of the encoded aspartate kinase protein according to SEQ ID NO: 20 with valine), lysC S301F (substitution of serine in position 301 of the encoded aspartate kinase protein according to SEQ ID NO: 20 with phenylalanine), lysC T308I (substitution of threonine in position 308 of the encoded aspartate kinase protein according to SEQ ID NO: 20 with isoleucine), lysC S301Y (substitution of serine in position 308 of the encoded aspartate kinase protein according to SEQ ID NO: 20 with tyrosine), lysC G345D (substitution of glycine in position 345 of the encoded aspartate kinase protein according to SEQ ID NO: 20 with asparaginic acid), lysC R320G (substitution of arginine in position 320 of the encoded aspartate kinase protein according to SEQ ID NO: 20 with glycine), lysC T311I (substitution of threonine in position 311 of the encoded aspartate kinase protein according to SEQ ID NO: 20 with isoleucine), lysC S381F (substitution of serine in position 381 of the encoded aspartate kinase protein according to SEQ ID NO: 20 with phenylalanine) and lysC S317A (substitution of serine in position 317 of the encoded aspartate kinase protein according to SEQ ID NO: 20 with alanine).

Particular preference is given to the lysC$^{FBR}$ allele lysC T311I (substitution of threonine in position 311 of the encoded aspartate kinase protein according to SEQ ID NO: 20 with isoleucine) and a lysC$^{FBR}$ allele comprising at least one substitution selected from the group consisting of A279T (substitution of alanine in position 279 of the encoded aspartate kinase protein according to SEQ ID NO: 20 with threonine) and S317A (substitution of serine in position 317 of the encoded aspartate kinase protein according to SEQ ID NO: 20 with alanine).

The strain DM1797, deposited with the DSMZ under the number DSM16833, harbors the lysC$^{FBR}$ allele lysC T311I. DM1797 is a mutant of *Corynebacterium glutamicum* ATCC 13032.

Starting from strain DM1797, a mutant referred to as DM1825, which harbors an opcA allele encoding an OpcA polypeptide in which L-histidine is present in position 107 of the amino acid sequence, L-asparagine is present in position 219, L-serine is present in position 233 and L-histidine is present in position 261, was isolated in the manner described above. The nucleotide sequence of the coding region of the opcA allele of the DM1825 mutant is depicted as SEQ ID NO: 7 and the amino acid sequence of the encoded polypeptide is depicted as SEQ ID NO: 8 and 10, respectively. SEQ ID NO: 7 comprises cytosine instead of thymine in position 319, thymine instead of cytosine in position 402, cytosine instead of thymine in position 600, cytosine instead of guanine in position 648, cytosine instead of adenine in position 657, thymine instead of cytosine in position 697 and cytosine instead of thymine in position 781. The phrase "cytosine instead of guanine in position 648"—and comparable phrases—means that the nucleobase guanine present in position 648 in the wild type sequence of the coding region (see SEQ ID NO: 1) has been replaced with cytosine (see SEQ ID NO: 7).

SEQ ID NO: 9 also indicates the nucleotide sequences located upstream and downstream of SEQ ID NO: 7.

In addition it is possible to use L-lysine-secreting coryneform bacteria which have an attenuated homoserine dehydrogenase or homoserine kinase or which possess other properties as known from the prior art.

L-Tryptophan-producing coryneform bacteria typically possess a feedback-resistant or desensibilized anthranilate synthase. The term feedback-resistant anthranilate synthase means anthranilate synthases which, compared to the wild type, have a lower sensitivity to inhibition (5 to 10%, 10% to 15% or 10% to 20%) by tryptophan or 5-fluoro-tryptophan (Matsui et al., Journal of Bacteriology 169 (11): 5330-5332 (1987)) or similar analogs. The genes or alleles encoding these desensibilized anthranilate synthases are also referred to as trpE$^{FBR}$ alleles. Examples of mutants or alleles of this kind are described, for example, in U.S. Pat. No. 6,180,373 and EP0338474.

The mutants obtained show increased secretion or production of the desired amino acid in a fermentation process, in comparison with the starting strain or parent strain employed.

The invention likewise relates to an isolated polynucleotide encoding an OpcA polypeptide of glucose 6-phosphate dehydrogenase, wherein the amino acid sequence of said polypeptide comprises one or more amino acids selected from the group consisting of:
  a) any proteinogenic amino acid other than L-tyrosine, preferably L-histidine, in position 107 of said amino acid sequence,
  b) any proteinogenic amino acid other than L-lysine, preferably L-asparagine, in position 219 of said amino acid sequence,
  c) any proteinogenic amino acid other than L-proline, preferably L-serine, in position 233 of said amino acid sequence, and
  d) any proteinogenic amino acid other than L-tyrosine, preferably L-histidine, in position 261 of said amino acid sequence.

The polynucleotide of the invention may be isolated from a mutant of the invention.

It is furthermore possible to use in-vitro methods for the mutagenesis of the opcA gene. The use of in-vitro methods involves subjecting isolated polynucleotides which comprise an opcA gene of a coryneform bacterium, preferably the Corynebacterium glutamicum wild type gene described in the prior art, to a mutagenic treatment.

The isolated polynucleotides may be, for example, isolated total DNA or chromosomal DNA or else amplicons of the opcA gene, which have been prepared with the aid of the polymerase chain reaction (PCR). Such amplicons are also referred to as PCR products; the term nucleic acid fragment can likewise be used. Instructions for the amplification of DNA sequences with the aid of the polymerase chain reaction can be found by the skilled worker, inter alia, in the manual by Gait: Oligonucleotide Synthesis: A Practical Approach (IRL Press, Oxford, UK, 1984) and Newton and Graham: PCR (Spektrum Akademischer Verlag, Heidelberg, Germany, 1994). It is likewise possible to incorporate the opcA gene to be mutagenized first into a vector, for example into a bacteriophage or into a plasmid.

Suitable methods of in-vitro mutagenesis are, inter alia, the treatment with hydroxylamine according to Miller (Miller, J. H.: A Short Course in Bacterial Genetics. A Laboratory Manual and Handbook for Escherichia coli and Related Bacteria, Cold Spring Harbor Laboratory Press, Cold Spring Harbor, 1992), the use of mutagenic oligonucleotides (T. A. Brown: Gentechnologie für Einsteiger [Genetic engineering for beginners], Spektrum Akademischer Verlag, Heidelberg, 1993 and R. M. Horton: PCR-Mediated Recombination and Mutagenesis, Molecular Biotechnology 3, 93-99 (1995)) and the use of a polymerase chain reaction using a DNA polymerase with a high error rate. An example of such a DNA polymerase is the Mutazyme DNA Polymerase (GeneMorph PCR Mutagenesis Kit, No. 600550) from Stratagene (La Jolla, Calif., USA).

Further instructions and reviews on the generation of mutations in vivo or in vitro can be found in the prior art and in known textbooks of genetics and molecular biology, such as, for example, the textbook by Knippers ("Molekulare Genetik", 6th edition, Georg Thieme Verlag, Stuttgart, Germany, 1995), that by Winnacker ("Gene and Klone", VCH Verlagsgesellschaft, Weinheim, Germany, 1990) or that by Hagemann ("Allgemeine Genetik", Gustav Fischer Verlag, Stuttgart, 1986).

The invention furthermore relates to an isolated polynucleotide encoding an OpcA polypeptide which comprises the amino acid sequence of SEQ ID NO: 2, said amino acid sequence comprising one or more of the amino acid substitutions selected from the group:
  a) substitution of L-tyrosine in position 107 with a different proteinogenic amino acid, preferably L-histidine,
  b) substitution of L-lysine in position 219 with a different proteinogenic amino acid, preferably L-asparagine,
  c) substitution of L-proline in position 233 with a different proteinogenic amino acid, preferably L-serine, and
  d) substitution of L-tyrosine in position 261 with a different proteinogenic amino acid, preferably L-histidine.

The invention furthermore relates to an isolated polynucleotide encoding an OpcA polypeptide which comprises an amino acid sequence having a length of 319 amino acids and comprising one or more of the amino acids selected from the group:
  a) any proteinogenic amino acid other than L-tyrosine, preferably L-histidine, in position 107,
  b) any proteinogenic amino acid other than L-lysine, preferably L-asparagine, in position 219,
  c) any proteinogenic amino acid other than L-proline, preferably L-serine, in position 233, and
  d) any proteinogenic amino acid other than L-tyrosine, preferably L-histidine, in position 261.

The invention furthermore relates to an isolated polynucleotide encoding an OpcA polypeptide which comprises, from positions 107 to 261 of the amino acid sequence, the amino acid sequence corresponding to positions 107 to 261 of SEQ ID NO: 6. The amino acid sequence of the encoded polypeptide preferably comprises an amino acid sequence corresponding to positions 98 to 270 of SEQ ID NO: 6 or positions 83 to 285 of SEQ ID NO: 6 or positions 63 to 305 of SEQ ID NO: 6 or positions 38 to 315 of SEQ ID NO:6 or positions 8 to 315 of SEQ ID NO:6 or positions 2 to 315 of SEQ ID NO:6 or positions 2 to 317 of SEQ ID NO:6 or positions 2 to 319 of SEQ ID NO:6. The length of the encoded polypeptide comprises very particularly preferably 319 amino acids.

The invention furthermore relates to an isolated polynucleotide encoding an OpcA polypeptide, wherein the amino acid sequence of said polypeptide has one or more amino acids selected from the group:
  a) any proteinogenic amino acid other than L-tyrosine, preferably L-histidine, in position 107 of said amino acid sequence,
  b) any proteinogenic amino acid other than L-lysine, preferably L-asparagine, in position 219 of said amino acid sequence,
  c) any proteinogenic amino acid other than L-proline, preferably L-serine, in position 233 of said amino acid sequence, and
  d) any proteinogenic amino acid other than L-tyrosine, preferably L-histidine, in position 261 of said amino acid sequence,
and comprising a nucleotide sequence identical to the nucleotide sequence of a polynucleotide which is obtainable by a polymerase chain reaction (PCR) using the primer pair whose nucleotide sequences comprise in each case at least 15 contiguous nucleotides selected from the nucleotide sequence between positions 1 and 334 of SEQ ID NO: 3 and from the complementary nucleotide sequence between positions 1600 and 1292 of SEQ ID NO: 3. An example of a suitable primer pair is depicted in SEQ ID NO: 11 and SEQ ID NO: 12. The preferred starting material (template DNA) is chromosomal DNA of coryneform bacteria which have been treated in particular with a mutagen. Particular preference is given to the chromosomal DNA of the genus *Corynebacterium* and very particular preference is given to that of the species *Corynebacterium glutamicum*.

The invention furthermore relates to an isolated polynucleotide hybridizing under stringent conditions to a nucleotide sequence complementary to SEQ ID NO: 5 or 7 and encoding an OpcA polypeptide whose amino acid sequence has one or more amino acids selected from the group:
 a) any proteinogenic amino acid other than L-tyrosine, preferably L-histidine, in position 107 of said amino acid sequence,
 b) any proteinogenic amino acid other than L-lysine, preferably L-asparagine, in position 219 of said amino acid sequence,
 c) any proteinogenic amino acid other than L-proline, preferably L-serine, in position 233 of said amino acid sequence, and
 d) any proteinogenic amino acid other than L-tyrosine, preferably L-histidine, in position 261 of said amino acid sequence.

Instructions regarding the hybridization of nucleic acids or polynucleotides can be found by the skilled worker, inter alia, in the manual "The DIG System User's Guide for Filter Hybridization" from Boehringer Mannheim GmbH (Mannheim, Germany, 1993) and in Liebl et al. (International Journal of Systematic Bacteriology 41: 255-260 (1991)). The hybridization is carried out under stringent conditions, i.e. only hybrids in which the probe, i.e. a polynucleotide comprising the nucleotide sequence complementary to SEQ ID NO:5, 7 or 9, and the target sequence, i.e. the polynucleotides treated or identified with the probe, are at least 90% identical, are formed. The stringency of the hybridization, including that of the washing steps, is known to be influenced or determined by varying the buffer composition, the temperature and the salt concentration. The hybridization reaction is generally carried out at relatively low stringency compared to the washing steps (Hybaid Hybridisation Guide, Hybaid Limited, Teddington, UK, 1996).

For example, a buffer corresponding to 5×SSC buffer at a temperature of approx. 50° C.-68° C. may be used for the hybridization reaction. In this case, probes may also hybridize with polynucleotides which are less than 90% identical to the nucleotide sequence of the probe employed. Such hybrids are less stable and are removed by washing under stringent conditions. This may be achieved, for example, by lowering the salt concentration to 2×SSC and, where appropriate, subsequently to 0.5×SSC (The DIG System User's Guide for Filter Hybridisation, Boehringer Mannheim, Mannheim, Germany, 1995), with the temperature being set to approx. 50° C.-68° C., approx. 52° C.-68° C., approx. 54° C.-68° C., approx. 56° C.-68° C., approx. 58° C.-68° C., approx. 60° C.-68° C., approx. 62° C.-68° C., approx. 64° C.-68° C., approx. 66° C.-68° C. Temperature ranges of approx. 64° C.-68° C. or approx. 66° C.-68° C. are preferred. It is possible, where appropriate, to lower the salt concentration down to a concentration corresponding to 0.2×SSC or 0.1×SSC. The SSC buffer comprises, where appropriate, sodium dodecyl sulfate (SDS) in a concentration of 0.1%. By gradually increasing the hybridization temperature in steps of approx. 1-2° C. from 50° C. to 68° C., it is possible to isolate polynucleotide fragments which have at least 90% or at least 91%, preferably at least 92% or at least 93% or at least 94% or at least 95% or at least 96%, and very particularly preferably at least 97% or at least 98% or at least 99%, identity to the sequence or complementary sequence of the probe employed and which encode an OpcA polypeptide which comprises the amino acid substitution of the invention. The nucleotide sequence of the polynucleotide obtained in this way is determined by known methods. Further instructions regarding hybridization are commercially available in the form of "kits" (e.g. DIG Easy Hyb from Roche Diagnostics GmbH, Mannheim, Germany, Catalog No. 1603558). The nucleotide sequences thus obtained encode OpcA polypeptides which are at least 90%, preferably at least 92% or at least 94% or at least 96%, and very particularly preferably at least 97% or at least 98% or at least 99%, identical to the amino acid sequence of SEQ ID NO: 6 or SEQ ID NO: 2 and which comprise one or more of the amino acid substitutions of the invention.

The invention furthermore relates to an isolated polynucleotide encoding an OpcA polypeptide, wherein the amino acid sequence of said polypeptide has one or more of the amino acids selected from the group
 a) any proteinogenic amino acid other than L-tyrosine, preferably L-histidine, in position 107 of said amino acid sequence,
 b) any proteinogenic amino acid other than L-lysine, preferably L-asparagine, in position 219 of said amino acid sequence,
 c) any proteinogenic amino acid other than L-proline, preferably L-serine, in position 233 of said amino acid sequence, and
 d) any proteinogenic amino acid other than L-tyrosine, preferably L-histidine, in position 261 of said amino acid sequence,
and comprising an amino acid sequence which moreover is at least 90%, preferably at least 92% or at least 94% or at least 96%, and very particularly preferably at least 97% or at least 98% or at least 99%, identical to the amino acid sequence of SEQ ID NO: 6 or SEQ ID NO: 2.

The invention furthermore relates to an isolated polynucleotide encoding an OpcA polypeptide, wherein the amino acid sequence of said polypeptide has one or more of the amino acids selected from the group:
 a) any proteinogenic amino acid other than L-tyrosine, preferably L-histidine, in position 107 of said amino acid sequence,
 b) any proteinogenic amino acid other than L-lysine, preferably L-asparagine, in position 219 of said amino acid sequence,
 c) any proteinogenic amino acid other than L-proline, preferably L-serine, in position 233 of said amino acid sequence, and
 d) any proteinogenic amino acid other than L-tyrosine, preferably L-histidine, in position 261 of said amino acid sequence,
and comprising a nucleotide sequence which moreover is at least 90%, preferably at least 92% or at least 94% or at least 96%, and very particularly preferably at least 97% or at least 98% or at least 99%, identical to the nucleotide sequence of SEQ ID NO: 5 or SEQ ID NO: 1.

An example of a polynucleotide encoding an OpcA polypeptide of the invention and having a nucleotide sequence which is at least 99% identical to that of SEQ ID NO: 5 is depicted in SEQ ID NO: 7. In addition to the nucleotide substitutions of thymine with cytosine in position 319, of adenine with cytosine in position 657, of cytosine with thymine in position 697 and of thymine with cytosine in position 781 (see SEQ ID NO: 5), the nucleotide sequence of this opcA allele has the nucleotide substitutions of cytosine with thymine in position 402, of thymine with cytosine in position 600 and of guanine with cytosine in position 648 (see SEQ ID NO: 7). The phrase "guanine with cytosine in position 648"—and comparable phrases—means that the nucleobase guanine present in position 648 of the wild type sequence of the coding region (see SEQ ID NO: 1) has been replaced with cytosine (see SEQ ID NO: 7).

The invention furthermore relates to an isolated polynucleotide encoding an OpcA polypeptide which comprises the amino acid sequence of SEQ ID NO: 6. The encoded polypeptide comprises, where appropriate, one (1) or more conservative amino acid substitution(s). Preferably, the polypeptide comprises no more than two (2), no more than three (3), no more than four (4) or no more than five (5), conservative amino acid substitutions.

The invention furthermore relates to an isolated polynucleotide encoding an opcA polypeptide which comprises the amino acid sequence SEQ ID NO: 6, including an extension at the N- or C-terminus by at least one (1) amino acid. This extension has no more than 50, 40, 30, 20, 10, 5, 3 or 2, amino acids or amino acid residues.

Finally, the invention also relates to opcA alleles encoding polypeptide variants of SEQ ID NO: 6, which comprise one or more insertions or deletions. These preferably comprise no more than 5, no more than 4, no more than 3 or no more than 2, insertions or deletions of amino acids.

The invention furthermore relates to an isolated polynucleotide comprising the nucleotide sequence according to SEQ ID NO: 5, 7 or 9.

Finally, the invention relates to an isolated polynucleotide comprising the opcA allele of the DM1825 mutant.

Moreover, the invention relates to an isolated polynucleotide comprising part of the coding region of an opcA allele of the invention, said isolated polynucleotide comprising in any case that part of the coding region which comprises one or more of the amino acid substitutions of the invention.

More specifically, a nucleic acid molecule or DNA fragment is comprised which encodes at least one amino acid sequence corresponding to positions 98 to 270 of SEQ ID NO: 2 or which encodes at least one amino acid sequence corresponding to positions 83 to 285 of SEQ ID NO: 2 or which encodes at least one amino acid sequence corresponding to positions 63 to 305 of SEQ ID NO: 2 or which encodes at least one amino acid sequence corresponding to positions 38 to 315 of SEQ ID NO: 2, with said amino acid sequence comprising one or more of the amino acid substitutions selected from the group:
 a) substitution of L-tyrosine in position 107 according to SEQ ID NO: 2 with a different proteinogenic amino acid, preferably L-histidine,
 b) substitution of L-lysine in position 219 according to SEQ ID NO: 2 with a different proteinogenic amino acid, preferably L-asparagine,
 c) substitution of L-proline in position 233 according to SEQ ID NO: 2 with a different proteinogenic amino acid, preferably L-serine, and
 d) substitution of L-tyrosine in position 261 according to SEQ ID NO: 2 with a different proteinogenic amino acid, preferably L-histidine.

Preference is given to nucleic acid molecules encoding at least one amino acid sequence corresponding to positions 98 to 270 of SEQ ID NO: 6, or at least corresponding to positions 83 to 285 of SEQ ID NO: 6, or at least corresponding to positions 63 to 305 of SEQ ID NO: 6, or at least corresponding to positions 38 to 315 of SEQ ID NO: 6, or at least corresponding to positions 8 to 315 of SEQ ID NO: 6.

The reading frame encoding the amino acid sequence corresponding to positions 98 to 270 of SEQ ID NO: 6 is likewise depicted as SEQ ID NO: 15. SEQ ID NO: 16 depicts the amino acid sequence encoded by said reading frame. Position 10 in SEQ ID NO: 16 corresponds to position 107 of SEQ ID NO: 2, 4, 6, 8 or 10. Position 122 in SEQ ID NO: 16 corresponds to position 219 of SEQ ID NO: 2, 4, 6, 8 or 10. Position 136 in SEQ ID NO: 16 corresponds to position 233 of SEQ ID NO: 2, 4, 6, 8 or 10. Position 164 in SEQ ID NO: 16 corresponds to position 261 of SEQ ID NO: 2, 4, 6, 8 or 10.

Very particular preference is given to nucleic acid molecules comprising at least one nucleotide sequence corresponding to positions 292 to 810 of SEQ ID NO: 5 or 7, or at least one nucleotide sequence corresponding to positions 247 to 855 of SEQ ID NO: 5 or 7, or at least one nucleotide sequence corresponding to positions 187 to 915 of SEQ ID NO: 5 or 7, or at least one nucleotide sequence corresponding to positions 112 to 948 of SEQ ID NO: 5 or 7, or at least one nucleotide sequence corresponding to positions 22 to 948 of SEQ ID NO: 5 or 7.

The reading frame corresponding to positions 292 to 810 of SEQ ID NO: 5 is depicted as SEQ ID NO: 15. The corresponding encoded amino acid sequence is depicted as SEQ ID NO: 16. The reading frame corresponding to positions 292 to 810 of SEQ ID NO: 7 is depicted as SEQ ID NO: 17. The corresponding encoded amino acid sequence is depicted as SEQ ID NO: 18.

In addition, the reading frames of the invention may comprise one or more mutations resulting in one or more conservative amino acid substitutions. The mutations preferably result in no more than 4%, no more than 2% or no more than 1%, conservative amino acid substitutions. The reading frames of the invention may furthermore comprise one or more silent mutations. The reading frames of the invention comprise preferably no more than 4%, and particularly preferably no more than 2% to no more than 1%, silent mutations.

The isolated polynucleotides of the invention may be used in order to produce recombinant strains of microorganisms, which release amino acids into the surrounding medium or accumulate them in the cell interior in an improved manner, compared to the starting or parent strain.

A widespread method of incorporating mutations into genes of coryneform bacteria is that of allele substitution which is also referred to as gene replacement. This process involves transferring a DNA fragment comprising the mutation of interest into the desired strain of a coryneform bacterium and incorporating said mutation into the chromosome of the desired strain by at least two recombination events or cross-over events or replacing the sequence of a gene in the strain in question with the mutated sequence.

Schwarzer and Pühler (Bio/Technology 9, 84-87 (1991)) used this method in order to incorporate a lysA allele carrying a deletion into the *C. glutamicum* chromosome, instead of the wild type gene. In the same way a lysA allele carrying an insertion was incorporated into the *C. glutamicum* chromosome, instead of the wild type gene. Schäfer et al. (Gene 145, 69-73 (1994)) employed said method in order to incorporate a deletion into the *C. glutamicum* hom-thrB operon. Nakagawa et al. (EP 1108790) and Ohnishi et al. (Applied Microbiology and Biotechnology 58(2), 217-223 (2002)) employed said method in order to incorporate various mutations, starting from the isolated alleles, into the *C. glutamicum* chromosome. In this way, Nakagawa et al. succeeded in incorporating a mutation referred to as Val59Ala into the homoserine dehydrogenase gene (hom), a mutation referred to as Thr311Ile into the aspartate kinase gene (lysC and ask, respectively), a mutation referred to as Pro458Ser into the pyruvate carboxylase gene (pyc) and a mutation referred to as Ala213Thr into the glucose 6-phosphate dehydrogenase gene (zwf) of *C. glutamicum* strains.

A process of the invention may use a polynucleotide of the invention, which comprises the entire coding region, as depicted, for example, in SEQ ID NO: 5 or 7, or which comprises part of the coding region, such as, for example, the nucleotide sequence encoding at least the amino acid sequence corresponding to positions 98 to 270 of SEQ ID NO: 6 and, respectively, 8, and depicted as SEQ ID NO: 15 and 17. The part of the coding region corresponding to at least SEQ ID NO: 15 or 17 is ≧519 nucleobases in length. Preference is given to those parts of the coding region whose length is ≧747 nucleobases, such as, for example, nucleic acid molecules encoding at least one amino acid sequence corresponding to positions 63 to 305 of SEQ ID NO: 6 and, respectively 8. Very particular preference is given to those parts of the coding region whose length is ≧834 nucleobases, such as, for example, nucleic acid molecules coding for at least one amino acid sequence corresponding to positions 38 to 315 of SEQ ID NO: 6 and, respectively, 8.

In said method, the DNA fragment comprising the mutation of interest is typically present in a vector, in particular a plasmid which preferably is replicated only to a limited extent, if at all, by the strain to be provided with the mutation. The auxiliary or intermediate host used, in which the vector can be replicated, is usually a bacterium of the genus *Escherichia*, preferably of the species *Escherichia coli*.

Examples of plasmid vectors of this kind are the pK*mob and pK*mobsacB vectors described by Schafer et al. (Gene 145, 69-73 (1994)), such as, for example, pK18mobsacB, and the vectors described in WO 02/070685 and WO 03/014362. These are replicative in *Escherichia coli* but not in coryneform bacteria. Particularly suitable are vectors comprising a gene with a conditionally negative-dominant action, such as, for example, the sacB gene (levansucrase gene) of *Bacillus*, for example, or the galK gene (galactose kinase gene) of *Escherichia coli*, for example. (A gene with conditionally negative-dominant action means a gene which, under certain conditions, is disadvantageous, for example toxic, to the host but which has, under different conditions, no adverse effects on the host carrying the gene.) Said vectors make possible the selection for recombination events in which the vector is eliminated from the chromosome. Nakamura et al. (U.S. Pat. No. 6,303,383) furthermore described a temperature-sensitive plasmid for coryneform bacteria, which can replicate only at temperatures below 31° C.

The vector is subsequently transferred to the coryneform bacterium by way of conjugation, for example by the method of Schafer (Journal of Bacteriology 172, 1663-1666 (1990)), or transformation, for example by the method of Dunican and Shivnan (Bio/Technology 7, 1067-1070 (1989)) or the method of Thierbach et al. (Applied Microbiology and Biotechnology 29, 356-362 (1988)). The DNA may also be transferred, where appropriate, by particle bombardment.

Incorporation of the mutation is achieved after homologous recombination by means of a first cross-over event causing integration and of a suitable second cross-over event causing excision in the target gene or in the target sequence, resulting in a recombinant bacterium.

The strains obtained may be identified and characterized by using, inter alia, the methods of Southern blotting hybridization, polymerase chain reaction, sequence determination, the method of fluorescence resonance energy transfer (FRET) (Lay et al. Clinical Chemistry 43, 2262-2267 (1997)) or methods of enzymology.

Accordingly, the invention further relates to a process for preparing a coryneform bacterium, which comprises
  a) transferring a polynucleotide of the invention to a coryneform bacterium,
  b) replacing the opcA gene which encodes an amino acid sequence with L-tyrosine in position 107, L-lysine in position Z19, L-proline in position 233 and L-tyrosine in position 261 and which is present in the chromosome of said coryneform bacterium with the polynucleotide of a), which encodes an amino acid sequence having one or more of the amino acids selected from the group consisting of:
    i) a different amino acid, preferably L-histidine, in position 107,
    ii) a different amino acid, preferably L-asparagine, in position 219,
    iii) a different amino acid, preferably L-serine, in position 233, and
    iv) a different amino acid, preferably L-serine, in position 261, and
  c) propagating the coryneform bacterium obtained by steps a) and b).

In this way a recombinant coryneform bacterium is obtained which comprises one (1) opcA allele of the invention, instead of the wild type opcA gene.

Another process of the invention for preparing a microorganism comprises
  a) transferring a polynucleotide of the invention, which encodes an opcA polypeptide, to a microorganism,
  b) replicating said polynucleotide in said microorganism, and
  c) propagating the microorganism obtained by steps a) and b).

In this way a recombinant microorganism is obtained, which comprises at least one (1) copy or several copies of a polynucleotide of the invention, which polynucleotide encodes an OpcA polypeptide, wherein the amino acid sequence of said polypeptide has one or more of the amino acids selected from the group consisting of:
  a) any proteinogenic amino acid other than L-tyrosine, preferably L-histidine, in position 107 of said amino acid sequence,
  b) any proteinogenic amino acid other than L-lysine, preferably L-asparagine, in position 219 of said amino acid sequence,
  c) any proteinogenic amino acid other than L-proline, preferably L-serine, in position 233 of said amino acid sequence, and
  d) any proteinogenic amino acid other than L-tyrosine, preferably L-histidine, in position 261 of said amino acid sequence.

Accordingly, the invention further relates to hosts or host cells, preferably microorganisms, particularly preferably coryneform bacteria and bacteria of the genus *Escherichia*, which comprise the polynucleotides of the invention. The invention likewise relates to microorganisms prepared by using the isolated polynucleotides. Such microorganisms or bacteria are also referred to as recombinant microorganisms or recombinant bacteria. In the same way, the invention relates to vectors comprising the polynucleotides of the invention. Finally, the invention likewise relates to hosts harboring said vectors.

The isolated polynucleotides of the invention may likewise be used for achieving overexpression of the polypeptides encoded by them.

Overexpression generally means an increase in the intracellular concentration or activity of a ribonucleic acid, a protein or an enzyme. In the case of the present invention, opcA alleles or polynucleotides which encode OpcA polypeptides are overexpressed, wherein the amino acid sequences of said polypeptide have one or more of the amino acids selected from the group consisting of:
  a) any proteinogenic amino acid other than L-tyrosine, preferably L-histidine, in position 107 of said amino acid sequence,
  b) any proteinogenic amino acid other than L-lysine, preferably L-asparagine, in position 219 of said amino acid sequence,
  c) any proteinogenic amino acid other than L-proline, preferably L-serine, in position 233 of said amino acid sequence, and d) any proteinogenic amino acid other than L-tyrosine, preferably L-histidine, in position 261 of said amino acid sequence.

Enzymes endogenous to the host-"aminopeptidases"—are known to be able to cleave N-terminal amino acids, in particular the N-terminal methionine, off the polypeptide produced.

Said increase in the concentration or activity of a gene product can be achieved, for example, by increasing the copy number of the corresponding polynucleotides by at least one copy.

A widespread method of increasing the copy number comprises incorporating the appropriate gene or allele into a vector, preferably a plasmid, which is replicated by a coryneform bacterium. Examples of suitable plasmid vectors are pZ1 (Menkel et al., Applied and Environmental Microbiology (1989) 64: 549-554) or the pSELF vectors described by Tauch et al. (Journal of Biotechnology 99, 79-91 (2002)). A review article on plasmids in *Corynebacterium glutamicum* can be found in Tauch et al. (Journal of Biotechnology 104, 27-40 (2003)).

Another common method of achieving overexpression is the process of chromosomal gene amplification. This method involves inserting at least one additional copy of the gene or allele of interest into the chromosome of a coryneform bacterium.

In one embodiment, as described, for example, for the hom-thrB operon in Reinscheid et al. (Applied and Environmental Microbiology 60, 126-132 (1994)), a plasmid which is non-replicative in *C. glutamicum* and which comprises the gene of interest is transferred to a coryneform bacterium. After homologous recombination by means of a cross-over event, the resulting strain comprises at least two copies of the gene or allele in question.

In another embodiment described in WO 03/040373 and US-2003-0219881-A1, one or more copies of the gene of interest are inserted at a desired site of the *C. glutamicum* chromosome by means of at least two recombination events. In this way, for example, a copy of a lysC allele encoding a L-lysine-insensitive aspartate kinase was incorporated into the *C. glutamicum* gluB gene.

In a further embodiment described in WO 03/014330 and US-2004-0043458-A1, at least one further copy of the gene of interest, preferably in tandem arrangement to the gene or allele already present, is incorporated by means of at least two recombination events at the natural locus. In this way it was possible, for example, to achieve a tandem duplication of a $lysC^{FBR}$ allele at the natural lysC gene locus.

Another method of achieving overexpression comprises linking the appropriate gene or allele functionally (operably linked) to a promoter or an expression cassette. Examples of suitable promoters for *Corynebacterium glutamicum* are described in the review article by Patek et al. (Journal of Biotechnology 104(1-3), 311-323 (2003)). It is furthermore possible to use the well-known promotors T3, T7, SP6, M13, lac, tac and trc described by Amann et al. (Gene 69(2), 301-315 (1988)) and Amann and Brosius (Gene 40(2-3), 183-190 (1985)). Such a promotor may be inserted, for example, upstream of the coding region of an opcA allele according to the invention, typically at a distance of approximately 1-500 or 1-334 nucleotides from the start codon, of a recombinant coryneform bacterium. A promotor of this kind may naturally likewise be inserted upstream of the opcA allele of a mutant of the invention. It is furthermore possible to link an isolated polynucleotide of the invention, which encodes a variant of the invention of opcA polypeptide, to a promotor and to incorporate the expression unit obtained into an extrachromosomally replicating plasmid or into the chromosome of a coryneform bacterium.

In addition, it is possible to mutate the promotor and regulatory regions or the ribosomal binding site which is located upstream of the structural gene. Measures of extending the mRNA lifetime likewise improve expression. Preventing the degradation of the enzyme protein furthermore likewise enhances enzyme activity. Alternatively, the gene or allele in question may furthermore be overexpressed by altering the media composition and the culturing process.

The overexpression measures increase the activity or concentration of the protein in question usually by at least 10%, 25%, 50%, 75%, 100%, 150%, 200%, 300%, 400% or 500%, up to no more than 1000% or 2000%, based on the activity or concentration of the protein in the starting microorganism or parent strain. A starting microorganism or parent strain means a microorganism which is subjected to the measures of the invention.

The concentration of the protein may be determined via 1- and 2-dimensional protein gel fractionation and subsequent optical identification of the protein concentration in the gel, using appropriate evaluation software. A common method of preparing the protein gels in the case of coryneform bacteria and of identifying the proteins is the procedure described by Hermann et al. (Electrophoresis, 22:1712-23 (2001)). The protein concentration may likewise be determined by Western blot hybridization using an antibody specific for the protein to be detected (Sambrook et al., Molecular cloning: a laboratory manual. $2^{nd}$ Ed. Cold Spring Harbor Laboratory Press, Cold Spring Harbor, N.Y., 1989) and subsequent optical evaluation using appropriate concentration determination software (Lohaus and Meyer (1998) Biospektrum 5:32-39; Lottspeich, Angewandte Chemie 321: 2630-2647 (1999)).

Accordingly, the invention relates to processes for overexpressing the OpcA polypeptides of the invention. A process of the invention for overexpression comprises, inter alia, increasing the copy number of a polynucleotide of the invention encoding an OpcA polypeptide variant having an amino acid sequence which comprises one or more of the amino acids selected from the group
  a) any proteinogenic amino acid other than L-tyrosine, preferably L-histidine, in position 107 of said amino acid sequence,
  b) any proteinogenic amino acid other than L-lysine, preferably L-asparagine, in position 219 of said amino acid sequence,
  c) any proteinogenic amino acid other than L-proline, preferably L-serine, in position 233 of said amino acid sequence, and
  d) any proteinogenic amino acid other than L-tyrosine, preferably L-histidine, in position 261 of said amino acid sequence, by at least one (1) or several copies. Another process of the invention comprises functionally linking a promoter to the polynucleotide.

The invention furthermore relates to microorganisms having an increased concentration of OpcA polypeptide of the invention in their cell interior. Where appropriate, said microorganisms have an increased glucose 6-phosphate dehydrogenase activity in their cell interior.

It may be additionally advantageous for improved production of L-amino acids to overexpress in the mutants or recombinant strains of the invention one or more enzymes of the particular biosynthetic pathway, of glycolysis, of anaplerotics, of the citrate cycle, of the pentose phosphate cycle, of the amino acid export and, where appropriate, regulatory proteins. Preference is usually given to the use of endogenous genes.

"Endogenous genes" or "endogenous nucleotide sequences" means the genes or the nucleotide sequences or alleles present in the population of a species.

Thus it is possible to overexpress for the preparation of L-lysine one or more of the genes selected from the group consisting of a dapA gene encoding a dihydrodipicolinate synthase, such as, for example, the *Corynebacterium glutamicum* wild type dapA gene described in EP 0 197 335, a zwf gene encoding a glucose 6-phosphate dehydrogenase, such as, for example, the *Corynebacterium glutamicum* wild type zwf gene described in JP-A-09224661 and EP-A-1108790, the *Corynebacterium glutamicum* zwf alleles described in US-2003-0175911-A1, which encode a protein in which, for example, the L-alanine in position 243 of the amino acid sequence has been replaced with L-threonine or in which the L-aspartic acid in position 245 has been replaced with L-serine, a pyc gene encoding a pyruvate carboxylase, such as, for example, the *Corynebacterium glutamicum* wild type pyc gene described in DE-A-198 31 609 and EP 1108790, the *Corynebacterium glutamicum* pyc allele described in EP 1 108 790, which encodes a protein in which L-proline in position 458 of the amino acid sequence has been replaced by L-serine, the *Corynebacterium glutamicum* pyc alleles described in WO 02/31158, which encode proteins which, according to claim 1, carry one or more of the amino acid substitutions selected from the group consisting of L-glutamic acid in position 153 replaced with L-aspartic acid, L-alanine in position 182 replaced with L-serine, L-alanine in position 206 replaced with L-serine, L-histidine in position 227 replaced with L-arginine, L-alanine in position 452 replaced with glycine and L-aspartic acid in position 1120 replaced with L-glutamic acid (FIG. 2A in WO 02/31158 specifies two different start positions for the pyruvate carboxylase, which positions differ by a length corresponding to 17 amino acids. Accordingly, position 153 in accordance with claim 1 in WO 02/31158 corresponds to position 170 in FIG. 2A in WO 02/31158, while position 182 in accordance with claim 1 corresponds to position 199 in FIG. 2A, position 206 in accordance with claim 1 corresponds to position 223 in FIG. 2A, position 227 in accordance with claim 1 corresponds to position 244 in FIG. 2A, position 452 in accordance with claim 1 corresponds to position 469 in FIG. 2A, position 1120 in accordance with claim 1 corresponds to position 1137 in FIG. 2B. FIG. 2A in WO 02/31158 furthermore indicates an amino acid substitution of A (alanine) with G (glycine) in position 472. Position 472 of the protein having the N terminal sequence MTA corresponds to position 455 of the protein having the N-terminal sequence MST according to FIG. 2A. FIG. 2B in WO 02/31158 furthermore indicates an amino acid substitution of D (aspartic acid) with E (glutamic acid) in position 1133 of the protein having the N-terminus MTA.), a lysC gene encoding an aspartate kinase, such as, for example, that of *Corynebacterium glutamicum* wild type lysC gene described as SEQ ID NO:281 in EP-A-1108790 (see also accession numbers AX120085 and 120365) and that of *Corynebacterium glutamicum* wild type of lysC gene, described as SEQ ID NO:25 in WO 01/00843 (see accession number AX063743), a lysC$^{FBR}$ allele, in particular according to Table 1, which encodes a feedback-resistant aspartate kinase variant, a lysE gene encoding a lysine export protein, such as, for example, the *Corynebacterium glutamicum* wild type lysE gene described in DE-A-195 48 222, the *Corynebacterium glutamicum* wild type zwa1 gene encoding the Zwa1 protein (U.S. Pat. No. 6,632,644).

In addition to using the alleles of the invention of the opcA gene, it may also be advantageous, for the purpose of producing L-lysine, to simultaneously attenuate or eliminate one or more of the endogenous genes selected from the group consisting of a pgi gene encoding glucose 6-phosphate isomerase, such as, for example, the *Corynebacterium glutamicum* pgi gene described in U.S. Pat. No. 6,586,214 and U.S. Pat. No. 6,465,238, a hom gene encoding homoserine dehydrogenase, such as, for example, the *Corynebacterium glutamicum* hom gene described in EP-A-0131171, a thrB gene encoding homoserine kinase, such as, for example, the *Corynebacterium glutamicum* thrB gene described by Peoples et al. (Molecular Microbiology 2 (1988): 63-72)), and a pfkB gene encoding phosphofructokinase, such as, for example, the *Corynebacterium glutamicum* pfkB gene described in WO 01/00844 (sequence no. 57).

In this connection, the term "attenuation" describes the reduction or elimination of the intracellular activity of one or more enzymes (proteins) which are encoded by the corresponding DNA in a microorganism which is achieved, for example, by using a weak promoter or using a gene or allele which encodes a corresponding enzyme having low activity, or inactivating the corresponding gene or enzyme (protein), and, where appropriate, combining these measures.

As a result of using the measures for achieving attenuation, the activity or concentration of the corresponding protein is generally lowered to from 0 to 75%, from 0 to 50%, from 0 to 25%, from 0 to 10%, or from 0 to 5%, of the activity or concentration of the wild type protein or of the activity or concentration of the protein in the starting microorganism.

Mutations which come into consideration for generating an attenuation are transitions, transversions, insertions and deletions of at least one (1) base pair or nucleotide. Depending on the effect which the amino acid substitution elicited by the mutation has on the enzyme activity, reference is made to missense mutations or nonsense mutations. A missense mutation leads to the replacement of a given amino acid in a protein with another amino acid, with the amino acid replacement constituting, in particular, a nonconservative amino acid substitution. This substitution impairs the efficiency or activity of the protein and reduces it down to a value of from 0 to 75%, from 0 to 50%, from 0 to 25%, from 0 to 10%, or from 0 to 5%.

A nonsense mutation leads to a stop codon being located in the coding region of the gene and consequently to translation being terminated prematurely. Insertions or deletions of at least one base pair in a gene lead to frame shift mutations which result in incorrect amino acids being incorporated or in the translation being terminated prematurely. If a stop codon is formed in the coding region as a consequence of mutation, this then also leads to translation being terminated prematurely.

Directions for generating such mutations belong to the prior art and are contained in known textbooks of genetics and molecular biology such as the textbook by Knippers ("Molekulare Genetik" [Molecular Genetics], 6$^{th}$ edition, Georg Thieme Verlag, Stuttgart, Germany, 1995), that by Winnacker ("Gene and Klone" [Genes and Clones], VCH Verlagsgesellschaft, Weinheim, Germany, 1990) or that by Hagemann ("Allgemeine Genetik" [General Genetics], Gustav Fischer Verlag, Stuttgart, 1986). Further measures are described in the prior art.

The isolated coryneform bacteria which are obtained by the measures of the invention exhibit a secretion or production of the desired amino acid, in a fermentation process, which is increased as compared with that of the starting strain or parent strain which was initially employed.

"Isolated bacteria" are to be understood as being the mutants and recombinant bacteria, in particular coryneform bacteria, according to the invention which are isolated or generated and which comprise an opcA allele encoding an OpcA polypeptide which comprises one or more of the amino acid substitutions described in positions 107, 219, 233 and 261.

The performance of the isolated bacteria, or of the fermentation process when using these bacteria, in regard to one or more of the parameters selected from the group comprising the product concentration (product per volume), the product yield (product formed per carbon source consumed) and the product formation (product formed per volume and time), or else of other process parameters and combinations thereof, is improved by at least 0.5%, at least 1%, at least 1.5%, or at least 2%, based on the starting strain or parent strain or the fermentation process when using these strains. The isolated coryneform bacteria according to the invention can be cultured continuously, as described, for example, in PCT/EP2004/008882, or discontinuously, in a batch process or a fed-batch process or a repeated fed-batch process, for the purpose of producing L-amino acids. A general summary of known culturing methods can be found in the textbook by Chmiel (Bioprozesstechnik 1. Einführung in die Bioverfahrenstechnik [Bioprocess Technology 1. Introduction to Bioprocess Technology] (Gustav Fischer Verlag, Stuttgart, 1991)) or in the textbook by Storhas (Bioreaktoren and periphere Einrichtungen [Bioreactors and Peripheral Equipment] (Vieweg Verlag, Brunswick/Wiesbaden, 1994)).

The culture medium or fermentation medium to be used must suitably satisfy the requirements of the given strains. Descriptions of media for culturing different microorganisms are given in the manual "Manual of Methods for General Bacteriology" published by the American Society for Bacteriology (Washington D.C., USA, 1981). The terms culture medium and fermentation medium or medium are mutually interchangeable.

The carbon source employed can be sugars and carbohydrates, such as glucose, sucrose, lactose, fructose, maltose, molasses, sucrose-containing solutions derived from sugar beet or sugar cane production, starch, starch hydrolysate and cellulose, oils and fats, such as soybean oil, sunflower oil, peanut oil and coconut oil, fatty acids, such as palmitic acid, stearic acid and linoleic acid, alcohols, such as glycerol, methanol and ethanol, and organic acids, such as acetic acid. These substances can be used individually or as mixtures.

The nitrogen source employed can be organic nitrogen-containing compounds, such as peptones, yeast extract, meat extract, malt extract, cornsteep liquor, soybean flour and urea, or inorganic compounds, such as ammonium sulfate, ammonium chloride, ammonium phosphate, ammonium carbonate and ammonium nitrate. The nitrogen sources can be used individually or as mixtures.

The phosphorus source employed can be phosphoric acid, potassium dihydrogen phosphate or dipotassium hydrogen phosphate or the corresponding sodium-containing salts.

The culture medium must furthermore contain salts, for example in the form of chlorides or sulfates of metals such as sodium, potassium, magnesium, calcium and iron, for example magnesium sulfate or iron sulfate, which are necessary for growth. Finally, essential growth substances, such as amino acids, for example homoserine, and vitamins, for example thiamine, biotin or pantothenic acid, can be used in addition to the abovementioned substances. In addition to this, suitable precursors of the respective amino acid can be added to the culture medium.

The abovementioned added substances can be added to the culture in the form of a once-only mixture or fed in a suitable manner during the culture.

Basic compounds such as sodium hydroxide, potassium hydroxide, ammonia or ammonia water, or acidic compounds such as phosphoric acid or sulfuric acid, are employed in a suitable manner for controlling the pH of the culture. In general, the pH is adjusted to a value of from 6.0 to 9.0, preferably of from 6.5 to 8. It is possible to use antifoamants, such as fatty acid polyglycol esters, for controlling foam formation. Suitable substances which act selectively, such as antibiotics, can be added to the medium in order to maintain the stability of plasmids. In order to maintain aerobic conditions, oxygen or oxygen-containing gas mixtures, such as air, are passed into the culture. It is also possible to use liquids which are enriched with hydrogen peroxide. Where appropriate, the fermentation is conducted under positive pressure, for example under a pressure of 0.03 to 0.2 MPa. The temperature of the culture is normally from 20° C. to 45° C., and preferably from 25° C. to 40° C. In the case of batch processes, the culture is continued until a maximum of the desired amino acid has been formed. This objective is normally achieved within from 10 hours to 160 hours. Longer culturing times are possible in the case of continuous processes.

Suitable fermentation media are described, inter alia, in U.S. Pat. No. 6,221,636, U.S. Pat. No. 5,840,551, U.S. Pat. No. 5,770,409, U.S. Pat. No. 5,605,818, U.S. Pat. No. 5,275,940 and U.S. Pat. No. 4,224,409.

Methods for determining L-amino acids are disclosed in the prior art. The analysis can, for example, take place by means of anion exchange chromatography, followed by ninhydrin derivatization, as described in Spackman et al. (Analytical Chemistry, 30 (1958), 1190), or it can take place by reversed phase HPLC, as described in Lindroth et al. (Analytical Chemistry (1979) 51: 1167-1174).

The invention accordingly relates to a process for preparing an L-amino acid, which comprises
   a) fermenting an isolated coryneform bacterium in a suitable medium, said bacterium comprising a gene encoding an OpcA polypeptide having one or more of the amino acids selected from the group consisting of
      a) any proteinogenic amino acid other than L-tyrosine, preferably L-histidine, in position 107 of said amino acid sequence, b) any proteinogenic amino acid other than L-lysine, preferably L-asparagine, in position 219 of said amino acid sequence,
c) any proteinogenic amino acid other than L-proline, preferably L-serine, in position 233 of said amino acid sequence, and
d) any proteinogenic amino acid other than L-tyrosine, preferably L-histidine, in position 261 of said amino acid sequence,
b) the L-amino acid being accumulated in the fermentation broth or in the cells of the isolated coryneform bacterium.

The fermentation broth which has been prepared in this way is then subjected to further processing into a solid or liquid product.

A fermentation broth is understood as being a fermentation medium in which a microorganism is cultured for a certain time and at a certain temperature. The fermentation medium, and/or the medium employed during the fermentation, contains/contain all the substances or components which ensure propagation of the microorganism and formation of the desired amino acid.

At the conclusion of the fermentation, the resulting fermentation broth accordingly contains a) the biomass of the microorganism which has been formed as a consequence of the propagation of the cells of the microorganism, b) the desired amino acid which has been formed during the fermentation, c) the organic by-products which have been formed during the fermentation, and d) the constituents of the fermentation medium/fermentation media employed, or the added substances, for example vitamins, such as biotin, amino acids, such as homoserine, or salts, such as magnesium sulfate, which were not consumed by the fermentation.

The organic by-products include substances which are produced by the microorganisms employed in the fermentation, where appropriate in addition to the given desired L-amino acid, and are secreted, where appropriate. These by-products include L-amino acids which amount to less than 30%, 20% or 10% compared with the desired amino acid. They also include organic acids which carry from one to three carboxyl groups, such as acetic acid, lactic acid, citric acid, malic acid or fumaric acid. Finally, they also include sugars, such as trehalose.

Typical fermentation broths which are suitable for industrial purposes have an amino acid content of from 40 g/kg to 180 g/kg or of from 50 g/kg to 150 g/kg. In general, the content of biomass (as dry biomass) is from 20 to 50 g/kg.

In the case of the amino acid L-lysine, essentially four different product forms have been disclosed in the prior art.

One group of L-lysine-containing products comprises concentrated, aqueous, alkaline solutions of purified L-lysine (EP-B-0534865). Another group, as described, for example, in U.S. Pat. No. 6,340,486 and U.S. Pat. No. 6,465,025, comprises aqueous, acidic, biomass-containing concentrates of L-lysine-containing fermentation broths. The best-known group of solid products comprises pulverulent or crystalline forms of purified or pure L-lysine, which is typically present in the form of a salt such as L-lysine monohydrochloride. Another group of solid product forms is described, for example, in EP-B-0533039. The product form which is described in this document contains, in addition to L-lysine, the major portion of the added substances which were used during the fermentative preparation, and which were not consumed, and, where appropriate, from >0% to 100% of the biomass of the microorganism employed.

In correspondence with the different product forms, a very wide variety of methods are known for collecting, isolating or purifying the L-amino acid from the fermentation broth for the purpose of preparing the L-amino acid-containing product or the purified L-amino acid.

It is essentially ion exchange chromatography methods, where appropriate using active charcoal, and crystallization methods which are used for preparing solid, pure L-amino acids. In the case of lysine, this results in the corresponding base or a corresponding salt such as the monohydrochloride (Lys-HCl) or the lysine sulfate ($Lys_2$-$H_2SO_4$).

As far as lysine is concerned, EP-B-0534865 describes a method for preparing aqueous, basic L-lysine-containing solutions from fermentation broths. In the method described therein, the biomass is separated off from the fermentation broth and discarded. A base such as sodium hydroxide, potassium hydroxide or ammonium hydroxide is used to adjust the pH to between 9 and 11. Following concentration and cooling, the mineral constituents (inorganic salts) are separated off from the broth by crystallization and either used as fertilizer or discarded.

In the case of processes for preparing lysine using the bacteria according to the invention, preference is given to those processes which result in products which contain constituents of the fermentation broth. These products are, in particular, used as animal feed additives.

Depending on the requirement, the biomass can be entirely or partially removed from the fermentation broth by means of separation methods such as centrifugation, filtration or decanting, or a combination of these methods, or all the biomass can be left in the fermentation broth. Where appropriate, the biomass, or the biomass-containing fermentation broth, is inactivated during a suitable process step, for example by means of thermal treatment (heating) or by means of adding acid.

In one approach, the biomass is completely or virtually completely removed, such that no (0%) or at most 30%, at most 20%, at most 10%, at most 5%, at most 1% or at most 0.1%, of the biomass remains in the prepared product. In another approach, the biomass is not removed, or only removed in trivial amounts, such that all (100%) or more than 70%, 80%, 90%, 95%, 99% or 99.9% of the biomass remains in the prepared product. In one process according to the invention, the biomass is accordingly removed in proportions of from $\geq 0\%$ to $\leq 100\%$.

Finally, the fermentation broth which is obtained after the fermentation can be adjusted, before or after the biomass has been completely or partially removed, to an acid pH using an inorganic acid, such as hydrochloric acid, sulfuric acid or phosphoric acid, or an organic acid, such as propionic acid (GB 1,439,728 or EP 1 331 220). It is likewise possible to acidify the fermentation broth when it contains the entire biomass (U.S. Pat. No. 6,340,486 or U.S. Pat. No. 6,465,025). Finally, the broth can also be stabilized by adding sodium bisulfite ($NaHSO_3$, GB 1,439,728) or another salt, for example an ammonium, alkali metal or alkaline earth metal salt of sulfurous acid.

Organic or inorganic solids which may be present in the fermentation broth are partially or entirely removed when the biomass is separated off. At least some (>0%), preferably at least 25%, particularly preferably at least 50%, and very particularly preferably at least 75%, of the organic by-products which are dissolved in the fermentation broth and the constituents of the fermentation medium (added substances), which are dissolved and not consumed remain in the product. Where appropriate, these by-products and constituents also remain completely (100%) or virtually completely, that is >95% or >98%, in the product. In this sense, the term "fermentation broth basis" means that a product comprises at least a part of the constituents of the fermentation broth.

Subsequently, water is extracted from the broth, or the broth is thickened or concentrated, using known methods, for example using a rotary evaporator, a thin-film evaporator or a falling-film evaporator, or by means of reverse osmosis or nanofiltration. This concentrated fermentation broth can then be worked up into flowable products, in particular into a finely divided powder or, preferably, a coarse-grained granulate, using methods of freeze drying, of spray drying or of spray granulation, or using other methods, for example in a circulating fluidized bed as described in PCT/EP2004/006655. Where appropriate, a desired product is isolated from the resulting granulate by means of screening or dust separation.

It is likewise possible to dry the fermentation broth directly, i.e. by spray drying or spray granulation without any prior concentration.

"Flowable" is understood as meaning powders which discharge unhindered from a series of glass discharge vessels having discharge apertures of different sizes, i.e. which discharge unhindered at least from the vessel having a 5 mm (millimeter) aperture (Klein: Seifen, Öle, Fette, Wachse [Soaps, Oils, Fats and Waxes] 94, 12 (1968)).

"Finely divided" means a powder the majority (>50%) of which has a particle size which is from 20 to 200 µm in diameter.

"Coarse-grained" means a product the majority (>50%) of which has a particle size of from 200 to 2000 µm in diameter.

The particle size can be determined using methods of laser diffraction spectrometry. The corresponding methods are described in the textbook "Teilchengrößenmessung in der Laborpraxis" [Particle Size Measurement in Laboratory Practice] by R. H. Müller and R. Schuhmann, Wissenschaftliche Verlagsgesellschaft Stuttgart (1996) or in the textbook "Introduction to Particle Technology" by M. Rhodes, Wiley & Sons (1998).

The flowable, finely divided powder can in turn be converted, by means of suitable compacting or granulating methods, into a coarse-grained, readily flowable, storable, and to a large extent dust-free, product.

The term "dust-free" means that the product only contains small proportions (<5%) of particle sizes of less than 100 µm in diameter.

Within the meaning of this invention, "storable" means a product which can be stored for at least one (1) year or longer, preferably at least 1.5 years or longer, particularly preferably two (2) years or longer, in a dry and cool environment without there being any significant loss (<5%) of the given amino acid.

The invention accordingly also relates to a process for preparing an L-amino acid-, preferably L-lysine- or L-tryptophan-, containing product, preferably an animal feed additive, from fermentation broths, which process is characterized by the steps of
  a) culturing and fermenting an L-amino acid-secreting coryneform bacterium which harbors at least one opcA allele encoding an OpcA polypeptide having one or more of the amino acids selected from the group consisting of
    a) any proteinogenic amino acid other than L-tyrosine, preferably L-histidine, in position 107 of said amino acid sequence,
    b) any proteinogenic amino acid other than L-lysine, preferably L-asparagine, in position 219 of said amino acid sequence,
    c) any proteinogenic amino acid other than L-proline, preferably L-serine, in position 233 of said amino acid sequence, and
    d) any proteinogenic amino acid other than L-tyrosine, preferably L-histidine, in position 261 of said amino acid sequence,
  in a fermentation medium,
  a) removing from 0 to 100% by weight of the biomass which is formed during the fermentation, and
  c) drying the fermentation broth which is obtained in accordance with a) and/or b) in order to obtain the product in the desired powder form or granulate form,
with, where appropriate, an acid selected from the group consisting of sulfuric acid, phosphoric acid or hydrochloric acid being added prior to step b) or c).

Preference is given to water being removed (concentration) from the L-amino acid-containing fermentation broth after step a) or b).

It is advantageous to use customary organic or inorganic auxiliary substances, or carrier substances such as starch, gelatin, cellulose derivatives or similar substances, as are customarily used as binders, gelatinizers or thickeners in foodstuff or feedstuff processing, or other substances, such as silicic acids, silicates (EP0743016A) or stearates, in connection with the granulation or compacting.

It is furthermore advantageous to provide the surface of the resulting granulates with oils, as described in WO 04/054381. The oils which can be used are mineral oils, vegetable oils or mixtures of vegetable oils. Examples of these oils are soybean oil, olive oil and soybean oil/lecithin mixtures. In the same way, silicone oils, polyethylene glycols or hydroxyethyl cellulose are also suitable. Treating the surfaces with said oils increases the abrasion resistance of the product and reduces the dust content. The content of oil in the product is from 0.02 to 2.0% by weight, preferably from 0.02 to 1.0% by weight, and very particularly preferably from 0.2 to 1.0% by weight, based on the total quantity of the feedstuff additives.

Preference is given to products having a content of 97% by weight of a particle size of from 100 to 1800 µm, or a content of 95% by weight of a particle size of from 300 to 1800 µm, in diameter. The content of dust, i.e. particles having a particle size of <100 µm, is preferably from >0 to 1% by weight, particularly preferably at most 0.5% by weight.

Alternatively, however, the product can also be absorbed onto an organic or inorganic carrier substance which is known and customary in feedstuff processing, for example silicic acids, silicates, grists, brans, meals, starches, sugars etc., and/or be mixed and stabilized with customary thickeners or binders. Application examples and methods in this regard are described in the literature (Die Mühle+Mischfuttertechnik [The Grinding Mill+Mixed Feed Technology] 132 (1995) 49, page 817).

Finally, the product can also be brought, by means of coating methods using film formers such as metal carbonates, silicic acids, silicates, alginates, stearates, starches, rubbers and cellulose ethers, as described in DE-C-4100920, into a state in which it is stable towards digestion by animal stomachs, in particular the ruminant stomach.

In order to set a desired amino acid concentration in the product, the appropriate amino acid can, depending on the requirement, be added during the process in the form of a concentrate or, where appropriate, of a largely pure substance or its salt in liquid or solid form. The latter can be added individually, or as mixtures, to the resulting fermentation broth, or to the concentrated fermentation broth, or else be added during the drying process or granulation process.

In the case of lysine, the ratio of the ions is adjusted during the preparation of lysine-containing products such that the ion ratio in accordance with the following formula $$2\times[SO_4^{2-}]+[Cl^-]-[NH_4^+]-[Na^+]-[K^+]-2\times[Ca^{2+}]/[L\text{-}Lys]$$

has a value of from 0.68 to 0.95, preferably of from 0.68 to 0.90, as described by Kushiki et al. in US 20030152633.

In the case of lysine, the solid fermentation broth-based product which has been prepared in this way has a lysine content (as lysine base) of from 10% by weight to 70% by weight or of from 20% by weight to 70% by weight, preferably of from 30% by weight to 70% by weight and very particularly preferably of from 40% by weight to 70% by weight, based on the dry mass of the product. It is also possible to achieve maximum contents of lysine base of 71% by weight, 72% by weight or 73% by weight.

In the case of an electrically neutral amino acid such as L-tryptophan, the solid fermentation broth-based product which has been prepared in this way has an amino acid content of at least 5% by weight, 10% by weight, 20% by weight or 30% by weight and maximally 50% by weight, 60% by weight, 70% by weight, 80% by weight, 90% by weight or up to 95% by weight.

The water content of the solid product is up to 5% by weight, preferably up to 4% by weight, and particularly preferably less than 3% by weight.

A mutant of *Corynebacterium glutamicum* which is designated DM1797 and which comprises the amino acid substitution lysC T311I in its aspartate kinase was deposited on Oct. 28, 2004 with the Deutsche Sammlung für Mikroorganismen und Zellkulturen [German Collection of Microorganisms and Cell Cultures] (DSMZ, Brunswick, Germany) as DSM 16833.

The *Corynebacterium glutamicum* mutant DM1825 of the invention, which comprises L-histidine in position 107, L-lysine in position 219, L-proline in position 233 and L-tyrosine in position 261 of the amino acid sequence of the OpcA polypeptide, was deposited on Apr. 5, 2005 with the Deutsche Sammlung für Mikroorganismen und Zellkulturen (DSMZ, Brunswick, Germany) as DSM 17223.

---

What is claimed is:

1. An isolated polynucleotide encoding (a) an OpcA polypeptide which is at least 90% identical to SEQ ID NO: 2 and contains any proteinogenic amino acid other than L-lysine at position 219 of SEQ ID NO: 2, wherein said OpcA polypeptide has glucose 6-phosphate dehydrogenase activity, or (b) an OpcA polypeptide which is at least 90% identical to SEQ ID NO: 2 and contains any proteinogenic amino acid other than L-lysine at position 107 of SEQ ID NO: 2, wherein said OpcA polypeptide has glucose 6-phosphate dehydrogenase activity.

2. The isolated polynucleotide of claim 1, wherein the amino acids at the following positions of the encoded protein are selected, individually or in combination, from the group consisting of:
 a) L-histidine in position 107,
 b) L-asparagine in position 219,
 c) L-serine in position 233, and
 a) L-histidine in position 261.

3. The isolated polynucleotide of claim 1, wherein the encoded polypeptide comprises 319 amino acids.

4. The isolated polynucleotide of claim 1, wherein positions 107 to 261 of the encoded polypeptide is replaced by positions 107 to 261 of SEQ ID NO: 6.

5. The isolated polynucleotide of claim 1, which is identical to the nucleotide sequence of a polynucleotide obtained by a polymerase chain reaction (PCR) using DNA obtained from a coryneform bacterium and using a primer pair consisting of a first primer comprising at least 15 contiguous nucleotides selected from the nucleotide sequence between positions 1 and 334 of SEQ ID NO: 3 and of a second primer comprising at least 15 contiguous nucleotides selected from the complementary nucleotide sequence between positions 1600 and 1292 of SEQ ID NO: 3.

6. The isolated polynucleotide of claim 1, which hybridizes with the nucleotide sequence complementary to SEQ ID NO: 5 under stringent conditions, said stringent conditions comprising a washing step using a buffer corresponding to 2×SSC at a temperature of from 52° C. to 68° C.

7. The isolated polynucleotide of claim 1, wherein the encoded polypeptide comprises an amino acid sequence which is at least 90% identical to the amino acid sequence of SEQ ID NO: 6 and has glucose 6-phosphate dehydrogenase activity.

8. The isolated polynucleotide of claim 1, which further comprises a nucleotide sequence which is at least 90% identical to the nucleotide sequence of SEQ ID NO: 5 or SEQ ID NO: 7.

9. The isolated polynucleotide of claim 1, wherein the encoded protein comprises an amino acid sequence selected from the group consisting of
 a) the amino acid sequence of SEQ ID NO: 6, and
 b) the amino acid sequence of SEQ ID NO: 6, including one or more conservative amino acid substitution(s), wherein said amino acid sequence contains any proteinogenic amino acid other than L-lysine at position 107 or 219 of SEQ ID NO: 6, wherein the encoded protein has glucose 6-phosphate dehydrogenase activity.

10. The isolated polynucleotide of claim 9, wherein the encoded polypeptide comprises the amino acid sequence of SEQ ID NO: 6.

11. The isolated polynucleotide of claim 8, wherein the nucleotide sequence comprises SEQ ID NO: 5 or SEQ ID NO: 7.

12. An isolated polynucleotide comprising a nucleic acid molecule which encodes (a) a polypeptide having an amino acid sequence as set forth in positions 98 to 270 of SEQ ID NO: 2, wherein the encoded polypeptide contains any proteinogenic amino acid other than L-lysine at position 219 of SEQ ID NO: 2, and has glucose 6-phosphate dehydrogenase activity, or (b) a polypeptide having an amino acid sequence as set forth in positions 98 to 270 of SEQ ID NO: 2, wherein the encoded polypeptide contains any proteinogenic amino acid other than L-lysine at position 107 of SEQ ID NO: 2, and has glucose 6-phosphate dehydrogenase activity.

13. The isolated polynucleotide of claim 12, wherein the amino acids at the following positions of the encoded protein are selected, individually or in combination, from the group consisting of:
 a) L-histidine in position 107,
 b) L-asparagine in position 219,
 c) L-serine in position 233, and
 d) L-histidine in position 261.

14. The isolated polynucleotide of claim 12, wherein at least one reading frame comprises the amino acid sequence as set forth in positions 98 to 270 of SEQ ID NO: 6.

15. The isolated polynucleotide of claim 12, wherein the amino acid sequence comprises conservative amino acid substitutions in one or more positions, except in positions 107, 219, 233 and 261.

16. The isolated polynucleotide of claim 12, which comprises one or more silent mutations, except in positions 107, 219, 233 and 261.

17. The isolated polynucleotide of claim 11, which comprises at least the nucleotide sequence corresponding to positions 292 to 810 of SEQ ID NO: 5 or SEQ ID NO: 7.

18. A process for preparing a recombinant *Coryneform* bacterium, which comprises
 a) transferring the isolated polynucleotide of claim 1 or 12 into a *Coryneform* bacterium,
 b) replacing the opcA gene which is present in the chromosome of said *Coryneform* bacterium with the isolated polynucleotide of step a), and
 c) propagating the *Coryneform* bacterium obtained by steps a) and b).

19. A process for preparing a recombinant microorganism, which comprises
 a) transferring the isolated polynucleotide of claim 1 or 12 into a microorganism,
 b) replicating said isolated polynucleotide in said microorganism, and
 c) propagating the microorganism obtained by steps a) and b).

20. A recombinant microorganism comprising the isolated polynucleotide of claim 1 or 12.

21. The recombinant microorganism of claim 20, which is a *Coryneform* bacterium or a bacterium of the genus *Escherichia*.

22. The recombinant microorganism of claim 21, wherein the *Coryneform* bacterium is the genus *Corynebacterium*.

23. The recombinant microorganism of claim 22, wherein the bacterium of the genus *Corynebacterium* is the species *Corynebacterium glutamicum*.

24. The recombinant microorganism of claim 22, wherein the *Corynebacterium* is a bacterium selected from the group consisting of *Corynebacterium efficiens, Corynebacterium glutamicum, Corynebacterium thermoaminogenes* and *Corynebacterium aminogenes*.

25. The recombinant microorganism of claim 22, which is an L-amino acid-secreting bacterium.

26. The recombinant microorganism of claim 22, which is an L-lysine or L-tryptophan-secreting bacterium.

27. The recombinant microorganism of claim 22, wherein the *Coryneform* bacterium is obtained by the following steps:
 a) treating a *Coryneform bacterium* capable of secreting amino acids with a mutagenic agent,
 b) isolating and propagating the mutant generated in a),
 c) providing nucleic acid from the mutant obtained in b),
 d) preparing a nucleic acid molecule, using the polymerase chain reaction, of the nucleic acid from c) and of a primer pair consisting of a first primer comprising at least 15 contiguous nucleotides selected from the nucleotide sequence between positions 1 and 334 of SEQ ID NO: 3 and a second primer comprising at least 15 contiguous nucleotides selected from the complementary nucleotide sequence between positions 1600 and 1292 of SEQ ID NO: 3,
 e) determining the nucleotide sequence of the nucleic acid molecule obtained in d) and determining the encoded amino acid sequence,
 f) comparing, where appropriate, the amino acid sequence determined in e) with SEQ ID NO: 6, and
 g) identifying a mutant comprising a polynucleotide which encodes a polypeptide comprising any proteinogenic amino acid other than L-lysine in position 107 or 219 of the amino acid sequence.

28. The recombinant microorganism of claim 27, wherein step b) is followed by selecting a mutant capable of secreting in a medium or accumulating in the cell interior at least 0.5% more of the desired L-amino acid than the *Coryneform* bacterium employed in step a) of claim 27.

29. A vector comprising the isolated polynucleotide of claim 1 or 12.

30. A recombinant microorganism comprising the vector of claim 29.

31. The recombinant microorganism of claim 30, which is a *Coryneform* bacterium or a bacterium of the genus *Escherichia*.

32. The recombinant microorganism of claim 31, wherein the *Coryneform* bacterium is the genus *Corynebacterium*.

33. The recombinant microorganism of claim 32, wherein the bacterium of the genus *Corynebacterium* is the species *Corynebacterium glutamicum*.

34. A process for overexpressing an OpcA polypeptide in a microorganism comprising increasing the copy number of the isolated polynucleotide of claim 1 or 12 in said microorganism by at least one copy.

35. A process for overexpressing an OpcA polypeptide in a microorganism comprising functionally linking a promoter or an expression cassette to the isolated polynucleotide of claim 1 or 12, and expressing the OpcA polypeptide in a microorganism.

36. A process for preparing an L-amino acid, which comprises
 a) fermenting the isolated *Corynebacterium* of claim 22 which contains (a) the isolated polynucleotide encoding an OpcA polypeptide which is at least 90% identical to SEQ ID NO: 2 and contains any proteinogenic amino acid other than L-lysine at position 219 of SEQ ID NO: 2, or (b) the isolated polynucleotide comprising a nucleic acid molecule which encodes at least one reading frame having an amino acid sequence as set forth in positions 98 to 270 of SEQ ID NO: 2, wherein the encoded polypeptide contains any proteinogenic amino acid other than L-lysine at position 219 of SEQ ID NO: 2, in a suitable medium, and
 b) increasing the concentration of the desired L-amino acid in the fermentation broth or in the cells of said bacterium.

37. The process of claim 36, which further comprises isolating or collecting the desired L-amino acid.

38. The process of claim 37, which further comprises purifying the desired L-amino acid.

39. The process of claim 36, which further comprises isolating or collecting the desired L-amino acid together with components of the fermentation broth and/or the biomass (>0 to 100%).

40. The process of claim 36, which further comprises
c) removing an amount of from 0 to 100% of the biomass produced from the fermentation broth obtained in step b) of claim 36, and
d) preparing from the broth obtained in step c) an essentially dry and shaped product by a method selected from the group consisting of granulation, compacting, spray drying and extrusion.

41. The process of claim 40, which further comprises adding an acid selected from the group consisting of sulfuric acid, hydrochloric acid and phosphoric acid to the fermentation broth prior to or after step c).

42. The process of claim 40, which further comprises removing water from the broth obtained prior to or after in step c).

43. The process of claim 40, which further comprises spraying the shaped product obtained in or during step d) with an oil.

* * * * *

SEQUENCE LISTING

```
<160> NUMBER OF SEQ ID NOS: 20

<210> SEQ ID NO 1
<211> LENGTH: 960
<212> TYPE: DNA
<213> ORGANISM: Corynebacterium glutamicum
<220> FEATURE:
<221> NAME/KEY: CDS
<222> LOCATION: (1)..(957)
<223> OTHER INFORMATION: opcA wild type gene

<400> SEQUENCE: 1 atg atc ttt gaa ctt ccg gat acc acc acc cag caa att tcc aag acc        48
Met Ile Phe Glu Leu Pro Asp Thr Thr Thr Gln Gln Ile Ser Lys Thr
1               5                   10                  15 cta act cga ctg cgt gaa tcg ggc acc cag gtc acc acc ggc cga gtg        96
Leu Thr Arg Leu Arg Glu Ser Gly Thr Gln Val Thr Thr Gly Arg Val
                20                  25                  30 ctc acc ctc atc gtg gtc act gac tcc gaa agc gat gtc gct gca gtt       144
Leu Thr Leu Ile Val Val Thr Asp Ser Glu Ser Asp Val Ala Ala Val
            35                  40                  45 acc gag tcc acc aat gaa gcc tcg cgc gag cac cca tct cgc gtg atc       192
Thr Glu Ser Thr Asn Glu Ala Ser Arg Glu His Pro Ser Arg Val Ile
        50                  55                  60 att ttg gtg gtt ggc gat aaa act gca gaa aac aaa gtt gac gca gaa       240
Ile Leu Val Val Gly Asp Lys Thr Ala Glu Asn Lys Val Asp Ala Glu
65                  70                  75                  80 gtc cgt atc ggt ggc gac gct ggt gct tcc gag atg atc atc atg cat       288
Val Arg Ile Gly Gly Asp Ala Gly Ala Ser Glu Met Ile Ile Met His
                85                  90                  95 ctc aac gga cct gtc gct gac aag ctc cag tat gtc gtc aca cca ctg       336
Leu Asn Gly Pro Val Ala Asp Lys Leu Gln Tyr Val Val Thr Pro Leu
                100                 105                 110 ttg ctt cct gac acc ccc atc gtt gct tgg tgg cca ggt gaa tca cca       384
Leu Leu Pro Asp Thr Pro Ile Val Ala Trp Trp Pro Gly Glu Ser Pro
            115                 120                 125 aag aat cct tcc cag gac cca att gga cgc atc gca caa cga cgc atc       432
Lys Asn Pro Ser Gln Asp Pro Ile Gly Arg Ile Ala Gln Arg Arg Ile
        130                 135                 140
```

| | | |
|---|---|---|
| act gat gct ttg tac gac cgt gat gac gca cta gaa gat cgt gtt gag<br>Thr Asp Ala Leu Tyr Asp Arg Asp Asp Ala Leu Glu Asp Arg Val Glu<br>145                   150                         155                   160 | | 480 |
| aac tat cac cca ggt gat acc gac atg acg tgg gcg cgc ctt acc cag<br>Asn Tyr His Pro Gly Asp Thr Asp Met Thr Trp Ala Arg Leu Thr Gln<br>                         165                         170                         175 | | 528 |
| tgg cgg gga ctt gtt gcc tcc tca ttg gat cac cca cac agc gaa<br>Trp Arg Gly Leu Val Ala Ser Ser Leu Asp His Pro Pro His Ser Glu<br>                 180                         185                         190 | | 576 |
| atc act tcc gtg agg ctg acc ggt gca agc ggc agt acc tcg gtg gat<br>Ile Thr Ser Val Arg Leu Thr Gly Ala Ser Gly Ser Thr Ser Val Asp<br>         195                        200                         205 | | 624 |
| ttg gct gca ggc tgg ttg gcg cgg agg ctg aaa gtg cct gtg atc cgc<br>Leu Ala Ala Gly Trp Leu Ala Arg Arg Leu Lys Val Pro Val Ile Arg<br>210                   215                         220 | | 672 |
| gag gtg aca gat gct ccc acc gtg cca acc gat gag ttt ggt act cca<br>Glu Val Thr Asp Ala Pro Thr Val Pro Thr Asp Glu Phe Gly Thr Pro<br>225                   230                         235                   240 | | 720 |
| ctg ctg gct atc cag cgc ctg gag atc gtt cgc acc acc ggc tcg atc<br>Leu Leu Ala Ile Gln Arg Leu Glu Ile Val Arg Thr Thr Gly Ser Ile<br>                         245                         250                         255 | | 768 |
| atc atc acc atc tat gac gct cat acc ctt cag gta gag atg ccg gaa<br>Ile Ile Thr Ile Tyr Asp Ala His Thr Leu Gln Val Glu Met Pro Glu<br>         260                        265                         270 | | 816 |
| tcc ggc aat gcc cca tcg ctg gtg gct att ggt cgt cga agt gag tcc<br>Ser Gly Asn Ala Pro Ser Leu Val Ala Ile Gly Arg Arg Ser Glu Ser<br>                 275                         280                         285 | | 864 |
| gac tgc ttg tct gag gag ctt cgc cac atg gat cca gat ttg ggc tac<br>Asp Cys Leu Ser Glu Glu Leu Arg His Met Asp Pro Asp Leu Gly Tyr<br>290                   295                         300 | | 912 |
| cag cac gca cta tcc ggc ttg tcc agc gtc aag ctg gaa acc gtc taa<br>Gln His Ala Leu Ser Gly Leu Ser Ser Val Lys Leu Glu Thr Val<br>305                   310                         315 | | 960 |

<210> SEQ ID NO 2
<211> LENGTH: 319
<212> TYPE: PRT
<213> ORGANISM: Corynebacterium glutamicum

<400> SEQUENCE: 2

Met Ile Phe Glu Leu Pro Asp Thr Thr Thr Gln Gln Ile Ser Lys Thr
1               5                   10                  15

Leu Thr Arg Leu Arg Glu Ser Gly Thr Gln Val Thr Thr Gly Arg Val
            20                  25                  30

Leu Thr Leu Ile Val Val Thr Asp Ser Glu Ser Asp Val Ala Ala Val
        35                  40                  45

Thr Glu Ser Thr Asn Glu Ala Ser Arg Glu His Pro Ser Arg Val Ile
    50                  55                  60

Ile Leu Val Val Gly Asp Lys Thr Ala Glu Asn Lys Val Asp Ala Glu
65                  70                  75                  80

Val Arg Ile Gly Gly Asp Ala Gly Ala Ser Glu Met Ile Ile Met His
                85                  90                  95

Leu Asn Gly Pro Val Ala Asp Lys Leu Gln Tyr Val Val Thr Pro Leu
            100                 105                 110

Leu Leu Pro Asp Thr Pro Ile Val Ala Trp Trp Pro Gly Glu Ser Pro
        115                 120                 125

Lys Asn Pro Ser Gln Asp Pro Ile Gly Arg Ile Ala Gln Arg Arg Ile
    130                 135                 140

-continued

```
Thr Asp Ala Leu Tyr Asp Arg Asp Asp Ala Leu Glu Asp Arg Val Glu
145                 150                 155                 160

Asn Tyr His Pro Gly Asp Thr Asp Met Thr Trp Ala Arg Leu Thr Gln
            165                 170                 175

Trp Arg Gly Leu Val Ala Ser Ser Leu Asp His Pro His Ser Glu
        180                 185                 190

Ile Thr Ser Val Arg Leu Thr Gly Ala Ser Gly Ser Thr Ser Val Asp
    195                 200                 205

Leu Ala Ala Gly Trp Leu Ala Arg Arg Leu Lys Val Pro Val Ile Arg
210                 215                 220

Glu Val Thr Asp Ala Pro Thr Val Pro Thr Asp Glu Phe Gly Thr Pro
225                 230                 235                 240

Leu Leu Ala Ile Gln Arg Leu Glu Ile Val Arg Thr Thr Gly Ser Ile
                245                 250                 255

Ile Ile Thr Ile Tyr Asp Ala His Thr Leu Gln Val Glu Met Pro Glu
            260                 265                 270

Ser Gly Asn Ala Pro Ser Leu Val Ala Ile Gly Arg Ser Glu Ser
        275                 280                 285

Asp Cys Leu Ser Glu Glu Leu Arg His Met Asp Pro Asp Leu Gly Tyr
290                 295                 300

Gln His Ala Leu Ser Gly Leu Ser Ser Val Lys Leu Glu Thr Val
305                 310                 315

<210> SEQ ID NO 3
<211> LENGTH: 1600
<212> TYPE: DNA
<213> ORGANISM: Corynebacterium glutamicum
<220> FEATURE:
<221> NAME/KEY: CDS
<222> LOCATION: (335)..(1291)
<223> OTHER INFORMATION: opcA wild type gene

<400> SEQUENCE: 3
gtgtgctcat ccgcttcggt tccaaggttc caggttctgc catggaagtc cgtgacgtca      60
acatggactt ctcctactca gaatccttca ctgaagaatc acctgaagca tacgagcgcc     120
tcattttgga tgcgctgtta gatgaatcca gcctcttccc taccaacgag gaagtggaac     180
tgagctggaa gattctggat ccaattcttg aagcatggga tgccgatgga gaaccagagg     240
attacccagc gggtacgtgg ggtccaaaga gcgctgatga aatgctttcc cgcaacggtc     300
acacctggcg caggccataa tttaggggca aaaa atg atc ttt gaa ctt ccg gat     355
                                    Met Ile Phe Glu Leu Pro Asp
                                      1               5 acc acc acc cag caa att tcc aag acc cta act cga ctg cgt gaa tcg     403
Thr Thr Thr Gln Gln Ile Ser Lys Thr Leu Thr Arg Leu Arg Glu Ser
        10                  15                  20 ggc acc cag gtc acc acc ggc cga gtg ctc acc ctc atc gtg gtc act     451
Gly Thr Gln Val Thr Thr Gly Arg Val Leu Thr Leu Ile Val Val Thr
    25                  30                  35 gac tcc gaa agc gat gtc gct gca gtt acc gag tcc acc aat gaa gcc     499
Asp Ser Glu Ser Asp Val Ala Ala Val Thr Glu Ser Thr Asn Glu Ala
40                  45                  50                  55 tcg cgc gag cac cca tct cgc gtg atc att ttg gtg gtt ggc gat aaa     547
Ser Arg Glu His Pro Ser Arg Val Ile Ile Leu Val Val Gly Asp Lys
                60                  65                  70 act gca gaa aac aaa gtt gac gca gaa gtc cgt atc ggt ggc gac gct     595
Thr Ala Glu Asn Lys Val Asp Ala Glu Val Arg Ile Gly Gly Asp Ala
            75                  80                  85
```

```
ggt gct tcc gag atg atc atc atg cat ctc aac gga cct gtc gct gac        643
Gly Ala Ser Glu Met Ile Ile Met His Leu Asn Gly Pro Val Ala Asp
         90                  95                 100 aag ctc cag tat gtc gtc aca cca ctg ttg ctt cct gac acc ccc atc        691
Lys Leu Gln Tyr Val Val Thr Pro Leu Leu Leu Pro Asp Thr Pro Ile
    105                 110                 115 gtt gct tgg tgg cca ggt gaa tca cca aag aat cct tcc cag gac cca        739
Val Ala Trp Trp Pro Gly Glu Ser Pro Lys Asn Pro Ser Gln Asp Pro
120                 125                 130                 135 att gga cgc atc gca caa cga cgc atc act gat gct ttg tac gac cgt        787
Ile Gly Arg Ile Ala Gln Arg Arg Ile Thr Asp Ala Leu Tyr Asp Arg
                140                 145                 150 gat gac gca cta gaa gat cgt gtt gag aac tat cac cca ggt gat acc        835
Asp Asp Ala Leu Glu Asp Arg Val Glu Asn Tyr His Pro Gly Asp Thr
            155                 160                 165 gac atg acg tgg gcg cgc ctt acc cag tgg cgg gga ctt gtt gcc tcc        883
Asp Met Thr Trp Ala Arg Leu Thr Gln Trp Arg Gly Leu Val Ala Ser
        170                 175                 180 tca ttg gat cac cca cca cac agc gaa atc act tcc gtg agg ctg acc        931
Ser Leu Asp His Pro Pro His Ser Glu Ile Thr Ser Val Arg Leu Thr
185                 190                 195 ggt gca agc ggc agt acc tcg gtg gat ttg gct gca ggc tgg ttg gcg        979
Gly Ala Ser Gly Ser Thr Ser Val Asp Leu Ala Ala Gly Trp Leu Ala
200                 205                 210                 215 cgg agg ctg aaa gtg cct gtg atc cgc gag gtg aca gat gct ccc acc       1027
Arg Arg Leu Lys Val Pro Val Ile Arg Glu Val Thr Asp Ala Pro Thr
                220                 225                 230 gtg cca acc gat gag ttt ggt act cca ctg ctg gct atc cag cgc ctg       1075
Val Pro Thr Asp Glu Phe Gly Thr Pro Leu Leu Ala Ile Gln Arg Leu
            235                 240                 245 gag atc gtt cgc acc acc ggc tcg atc atc atc acc atc tat gac gct       1123
Glu Ile Val Arg Thr Thr Gly Ser Ile Ile Ile Thr Ile Tyr Asp Ala
        250                 255                 260 cat acc ctt cag gta gag atg ccg gaa tcc ggc aat gcc cca tcg ctg       1171
His Thr Leu Gln Val Glu Met Pro Glu Ser Gly Asn Ala Pro Ser Leu
    265                 270                 275 gtg gct att ggt cgt cga agt gag tcc gac tgc ttg tct gag gag ctt       1219
Val Ala Ile Gly Arg Arg Ser Glu Ser Asp Cys Leu Ser Glu Glu Leu
280                 285                 290                 295 cgc cac atg gat cca gat ttg ggc tac cag cac gca cta tcc ggc ttg       1267
Arg His Met Asp Pro Asp Leu Gly Tyr Gln His Ala Leu Ser Gly Leu
                300                 305                 310 tcc agc gtc aag ctg gaa acc gtc taaggagaaa tacaacacta tggttgatgt      1321
Ser Ser Val Lys Leu Glu Thr Val
            315 agtacgcgca cgcgatactg aagatttggt tgcacaggct gcctccaaat tcattgaggt    1381 tgttgaagca gcaactgcca ataatggcac cgcacaggta gtgctcaccg gtggtggcgc    1441 cggcatcaag ttgctggaaa agctcagcgt tgatgcggct gaccttgcct gggatcgcat    1501 tcatgtgttc ttcggcgatg agcgcaatgt ccctgtcagt gattctgagt ccaatgaggg    1561 ccaggctcgt gaggcactgt tgtccaaggt ttctatccc                           1600

<210> SEQ ID NO 4
<211> LENGTH: 319
<212> TYPE: PRT
<213> ORGANISM: Corynebacterium glutamicum
```

<400> SEQUENCE: 4

```
Met Ile Phe Glu Leu Pro Asp Thr Thr Thr Gln Gln Ile Ser Lys Thr
1               5                   10                  15

Leu Thr Arg Leu Arg Glu Ser Gly Thr Gln Val Thr Thr Gly Arg Val
            20                  25                  30

Leu Thr Leu Ile Val Val Thr Asp Ser Glu Ser Asp Val Ala Ala Val
        35                  40                  45

Thr Glu Ser Thr Asn Glu Ala Ser Arg Glu His Pro Ser Arg Val Ile
    50                  55                  60

Ile Leu Val Val Gly Asp Lys Thr Ala Glu Asn Lys Val Asp Ala Glu
65                  70                  75                  80

Val Arg Ile Gly Gly Asp Ala Gly Ala Ser Glu Met Ile Ile Met His
                85                  90                  95

Leu Asn Gly Pro Val Ala Asp Lys Leu Gln Tyr Val Val Thr Pro Leu
            100                 105                 110

Leu Leu Pro Asp Thr Pro Ile Val Ala Trp Pro Gly Glu Ser Pro
        115                 120                 125

Lys Asn Pro Ser Gln Asp Pro Ile Gly Arg Ile Ala Gln Arg Arg Ile
130                 135                 140

Thr Asp Ala Leu Tyr Asp Arg Asp Ala Leu Glu Asp Arg Val Glu
145                 150                 155                 160

Asn Tyr His Pro Gly Asp Thr Asp Met Thr Trp Ala Arg Leu Thr Gln
                165                 170                 175

Trp Arg Gly Leu Val Ala Ser Ser Leu Asp His Pro Pro His Ser Glu
            180                 185                 190

Ile Thr Ser Val Arg Leu Thr Gly Ala Ser Gly Ser Thr Ser Val Asp
        195                 200                 205

Leu Ala Ala Gly Trp Leu Ala Arg Arg Leu Lys Val Pro Val Ile Arg
210                 215                 220

Glu Val Thr Asp Ala Pro Thr Val Pro Thr Asp Glu Phe Gly Thr Pro
225                 230                 235                 240

Leu Leu Ala Ile Gln Arg Leu Glu Ile Val Arg Thr Thr Gly Ser Ile
                245                 250                 255

Ile Ile Thr Ile Tyr Asp Ala His Thr Leu Gln Val Glu Met Pro Glu
            260                 265                 270

Ser Gly Asn Ala Pro Ser Leu Val Ala Ile Gly Arg Ser Glu Ser
        275                 280                 285

Asp Cys Leu Ser Glu Glu Leu Arg His Met Asp Pro Asp Leu Gly Tyr
290                 295                 300

Gln His Ala Leu Ser Gly Leu Ser Ser Val Lys Leu Glu Thr Val
305                 310                 315
```

```
<210> SEQ ID NO 5
<211> LENGTH: 960
<212> TYPE: DNA
<213> ORGANISM: Corynebacterium glutamicum
<220> FEATURE:
<221> NAME/KEY: CDS
<222> LOCATION: (1)..(957)
<223> OTHER INFORMATION: opcA allele
<220> FEATURE:
<221> NAME/KEY: mutation
<222> LOCATION: (319)..(319)
<223> OTHER INFORMATION: T -> C transition
<220> FEATURE:
<221> NAME/KEY: mutation
<222> LOCATION: (657)..(657)
<223> OTHER INFORMATION: A -> C transversion
```

```
<220> FEATURE:
<221> NAME/KEY: mutation
<222> LOCATION: (697)..(697)
<223> OTHER INFORMATION: C -> T transition
<220> FEATURE:
<221> NAME/KEY: mutation
<222> LOCATION: (781)..(781)
<223> OTHER INFORMATION: T -> C transition

<400> SEQUENCE: 5 atg atc ttt gaa ctt ccg gat acc acc acc cag caa att tcc aag acc      48
Met Ile Phe Glu Leu Pro Asp Thr Thr Thr Gln Gln Ile Ser Lys Thr
  1               5                  10                  15 cta act cga ctg cgt gaa tcg ggc acc cag gtc acc acc ggc cga gtg      96
Leu Thr Arg Leu Arg Glu Ser Gly Thr Gln Val Thr Thr Gly Arg Val
             20                  25                  30 ctc acc ctc atc gtg gtc act gac tcc gaa agc gat gtc gct gca gtt     144
Leu Thr Leu Ile Val Val Thr Asp Ser Glu Ser Asp Val Ala Ala Val
         35                  40                  45 acc gag tcc acc aat gaa gcc tcg cgc gag cac cca tct cgc gtg atc     192
Thr Glu Ser Thr Asn Glu Ala Ser Arg Glu His Pro Ser Arg Val Ile
 50                  55                  60 att ttg gtg gtt ggc gat aaa act gca gaa aac aaa gtt gac gca gaa     240
Ile Leu Val Val Gly Asp Lys Thr Ala Glu Asn Lys Val Asp Ala Glu
 65                  70                  75                  80 gtc cgt atc ggt ggc gac gct ggt gct tcc gag atg atc atc atg cat     288
Val Arg Ile Gly Gly Asp Ala Gly Ala Ser Glu Met Ile Ile Met His
                 85                  90                  95 ctc aac gga cct gtc gct gac aag ctc cag cat gtc gtc aca cca ctg     336
Leu Asn Gly Pro Val Ala Asp Lys Leu Gln His Val Val Thr Pro Leu
            100                 105                 110 ttg ctt cct gac acc ccc atc gtt gct tgg tgg cca ggt gaa tca cca     384
Leu Leu Pro Asp Thr Pro Ile Val Ala Trp Trp Pro Gly Glu Ser Pro
        115                 120                 125 aag aat cct tcc cag gac cca att gga cgc atc gca caa cga cgc atc     432
Lys Asn Pro Ser Gln Asp Pro Ile Gly Arg Ile Ala Gln Arg Arg Ile
    130                 135                 140 act gat gct ttg tac gac cgt gat gac gca cta gaa gat cgt gtt gag     480
Thr Asp Ala Leu Tyr Asp Arg Asp Asp Ala Leu Glu Asp Arg Val Glu
145                 150                 155                 160 aac tat cac cca ggt gat acc gac atg acg tgg gcg cgc ctt acc cag     528
Asn Tyr His Pro Gly Asp Thr Asp Met Thr Trp Ala Arg Leu Thr Gln
                165                 170                 175 tgg cgg gga ctt gtt gcc tcc tca ttg gat cac cca cca cac agc gaa     576
Trp Arg Gly Leu Val Ala Ser Ser Leu Asp His Pro Pro His Ser Glu
            180                 185                 190 atc act tcc gtg agg ctg acc ggt gca agc ggc agt acc tcg gtg gat     624
Ile Thr Ser Val Arg Leu Thr Gly Ala Ser Gly Ser Thr Ser Val Asp
        195                 200                 205 ttg gct gca ggc tgg ttg gcg cgg agg ctg aac gtg cct gtg atc cgc     672
Leu Ala Ala Gly Trp Leu Ala Arg Arg Leu Asn Val Pro Val Ile Arg
    210                 215                 220 gag gtg aca gat gct ccc acc gtg tca acc gat gag ttt ggt act cca     720
Glu Val Thr Asp Ala Pro Thr Val Ser Thr Asp Glu Phe Gly Thr Pro
225                 230                 235                 240 ctg ctg gct atc cag cgc ctg gag atc gtt cgc acc acc ggc tcg atc     768
Leu Leu Ala Ile Gln Arg Leu Glu Ile Val Arg Thr Thr Gly Ser Ile
                245                 250                 255 atc atc acc atc cat gac gct cat acc ctt cag gta gag atg ccg gaa     816
Ile Ile Thr Ile His Asp Ala His Thr Leu Gln Val Glu Met Pro Glu
            260                 265                 270
```

```
tcc ggc aat gcc cca tcg ctg gtg gct att ggt cgt cga agt gag tcc      864
Ser Gly Asn Ala Pro Ser Leu Val Ala Ile Gly Arg Arg Ser Glu Ser
        275                 280                 285 gac tgc ttg tct gag gag ctt cgc cac atg gat cca gat ttg ggc tac      912
Asp Cys Leu Ser Glu Glu Leu Arg His Met Asp Pro Asp Leu Gly Tyr
    290                 295                 300 cag cac gca cta tcc ggc ttg tcc agc gtc aag ctg gaa acc gtc taa      960
Gln His Ala Leu Ser Gly Leu Ser Ser Val Lys Leu Glu Thr Val
305                 310                 315
```

<210> SEQ ID NO 6
<211> LENGTH: 319
<212> TYPE: PRT
<213> ORGANISM: Corynebacterium glutamicum

<400> SEQUENCE: 6

```
Met Ile Phe Glu Leu Pro Asp Thr Thr Gln Gln Ile Ser Lys Thr
1               5                   10                  15

Leu Thr Arg Leu Arg Glu Ser Gly Thr Gln Val Thr Thr Gly Arg Val
        20                  25                  30

Leu Thr Leu Ile Val Val Thr Asp Ser Glu Ser Asp Val Ala Ala Val
        35                  40                  45

Thr Glu Ser Thr Asn Glu Ala Ser Arg Glu His Pro Ser Arg Val Ile
    50                  55                  60

Ile Leu Val Val Gly Asp Lys Thr Ala Glu Asn Lys Val Asp Ala Glu
65                  70                  75                  80

Val Arg Ile Gly Gly Asp Ala Gly Ala Ser Glu Met Ile Ile Met His
                85                  90                  95

Leu Asn Gly Pro Val Ala Asp Lys Leu Gln His Val Val Thr Pro Leu
            100                 105                 110

Leu Leu Pro Asp Thr Pro Ile Val Ala Trp Trp Pro Gly Glu Ser Pro
        115                 120                 125

Lys Asn Pro Ser Gln Asp Pro Ile Gly Arg Ile Ala Gln Arg Arg Ile
    130                 135                 140

Thr Asp Ala Leu Tyr Asp Arg Asp Asp Ala Leu Glu Asp Arg Val Glu
145                 150                 155                 160

Asn Tyr His Pro Gly Asp Thr Asp Met Thr Trp Ala Arg Leu Thr Gln
                165                 170                 175

Trp Arg Gly Leu Val Ala Ser Ser Leu Asp His Pro Pro His Ser Glu
            180                 185                 190

Ile Thr Ser Val Arg Leu Thr Gly Ala Ser Gly Ser Thr Ser Val Asp
        195                 200                 205

Leu Ala Ala Gly Trp Leu Ala Arg Arg Leu Asn Val Pro Val Ile Arg
    210                 215                 220

Glu Val Thr Asp Ala Pro Thr Val Ser Thr Asp Glu Phe Gly Thr Pro
225                 230                 235                 240

Leu Leu Ala Ile Gln Arg Leu Glu Ile Val Arg Thr Thr Gly Ser Ile
                245                 250                 255

Ile Ile Thr Ile His Asp Ala His Thr Leu Gln Val Glu Met Pro Glu
            260                 265                 270

Ser Gly Asn Ala Pro Ser Leu Val Ala Ile Gly Arg Arg Ser Glu Ser
        275                 280                 285

Asp Cys Leu Ser Glu Glu Leu Arg His Met Asp Pro Asp Leu Gly Tyr
    290                 295                 300

Gln His Ala Leu Ser Gly Leu Ser Ser Val Lys Leu Glu Thr Val
305                 310                 315
```

```
<210> SEQ ID NO 7
<211> LENGTH: 960
<212> TYPE: DNA
<213> ORGANISM: Corynebacterium glutamicum
<220> FEATURE:
<221> NAME/KEY: CDS
<222> LOCATION: (1)..(957)
<223> OTHER INFORMATION: opcA allele
<220> FEATURE:
<221> NAME/KEY: mutation
<222> LOCATION: (319)..(319)
<223> OTHER INFORMATION: T -> C transition
<220> FEATURE:
<221> NAME/KEY: mutation
<222> LOCATION: (402)..(402)
<223> OTHER INFORMATION: C -> T transition
<220> FEATURE:
<221> NAME/KEY: mutation
<222> LOCATION: (600)..(600)
<223> OTHER INFORMATION: T -> C transition
<220> FEATURE:
<221> NAME/KEY: mutation
<222> LOCATION: (648)..(648)
<223> OTHER INFORMATION: G -> C transversion
<220> FEATURE:
<221> NAME/KEY: mutation
<222> LOCATION: (657)..(657)
<223> OTHER INFORMATION: A -> C transversion
<220> FEATURE:
<221> NAME/KEY: mutation
<222> LOCATION: (697)..(697)
<223> OTHER INFORMATION: C -> T transition
<220> FEATURE:
<221> NAME/KEY: mutation
<222> LOCATION: (781)..(781)
<223> OTHER INFORMATION: T -> C transition

<400> SEQUENCE: 7 atg atc ttt gaa ctt ccg gat acc acc acc cag caa att tcc aag acc    48
Met Ile Phe Glu Leu Pro Asp Thr Thr Thr Gln Gln Ile Ser Lys Thr
 1               5                  10                  15 cta act cga ctg cgt gaa tcg ggc acc cag gtc acc acc ggc cga gtg    96
Leu Thr Arg Leu Arg Glu Ser Gly Thr Gln Val Thr Thr Gly Arg Val
             20                  25                  30 ctc acc ctc atc gtg gtc act gac tcc gaa agc gat gtc gct gca gtt   144
Leu Thr Leu Ile Val Val Thr Asp Ser Glu Ser Asp Val Ala Ala Val
         35                  40                  45 acc gag tcc acc aat gaa gcc tcg cgc gag cac cca tct cgc gtg atc   192
Thr Glu Ser Thr Asn Glu Ala Ser Arg Glu His Pro Ser Arg Val Ile
     50                  55                  60 att ttg gtg gtt ggc gat aaa act gca gaa aac aaa gtt gac gca gaa   240
Ile Leu Val Val Gly Asp Lys Thr Ala Glu Asn Lys Val Asp Ala Glu
 65                  70                  75                  80 gtc cgt atc ggt ggc gac gct ggt gct tcc gag atg atc atc atg cat   288
Val Arg Ile Gly Gly Asp Ala Gly Ala Ser Glu Met Ile Ile Met His
                 85                  90                  95 ctc aac gga cct gtc gct gac aag ctc cag cat gtc gtc aca cca ctg   336
Leu Asn Gly Pro Val Ala Asp Lys Leu Gln His Val Val Thr Pro Leu
            100                 105                 110 ttg ctt cct gac acc ccc atc gtt gct tgg tgg cca ggt gaa tca cca   384
Leu Leu Pro Asp Thr Pro Ile Val Ala Trp Trp Pro Gly Glu Ser Pro
        115                 120                 125 aag aat cct tcc cag gat cca att gga cgc atc gca caa cga cgc atc   432
Lys Asn Pro Ser Gln Asp Pro Ile Gly Arg Ile Ala Gln Arg Arg Ile
    130                 135                 140 act gat gct ttg tac gac cgt gat gac gca cta gaa gat cgt gtt gag   480
Thr Asp Ala Leu Tyr Asp Arg Asp Asp Ala Leu Glu Asp Arg Val Glu
145                 150                 155                 160
```

```
aac tat cac cca ggt gat acc gac atg acg tgg gcg cgc ctt acc cag    528
Asn Tyr His Pro Gly Asp Thr Asp Met Thr Trp Ala Arg Leu Thr Gln
            165                 170                 175 tgg cgg gga ctt gtt gcc tcc tca ttg gat cac cca cac agc gaa        576
Trp Arg Gly Leu Val Ala Ser Ser Leu Asp His Pro His Ser Glu
        180                 185                 190 atc act tcc gtg agg ctg acc ggc gca agc ggc agt acc tcg gtg gat    624
Ile Thr Ser Val Arg Leu Thr Gly Ala Ser Gly Ser Thr Ser Val Asp
        195                 200                 205 ttg gct gca ggc tgg ttg gcg cgc agg ctg aac gtg cct gtg atc cgc    672
Leu Ala Ala Gly Trp Leu Ala Arg Arg Leu Asn Val Pro Val Ile Arg
    210                 215                 220 gag gtg aca gat gct ccc acc gtg tca acc gat gag ttt ggt act cca    720
Glu Val Thr Asp Ala Pro Thr Val Ser Thr Asp Glu Phe Gly Thr Pro
225                 230                 235                 240 ctg ctg gct atc cag cgc ctg gag atc gtt cgc acc acc ggc tcg atc    768
Leu Leu Ala Ile Gln Arg Leu Glu Ile Val Arg Thr Thr Gly Ser Ile
            245                 250                 255 atc atc acc atc cat gac gct cat acc ctt cag gta gag atg ccg gaa    816
Ile Ile Thr Ile His Asp Ala His Thr Leu Gln Val Glu Met Pro Glu
            260                 265                 270 tcc ggc aat gcc cca tcg ctg gtg gct att ggt cgt cga agt gag tcc    864
Ser Gly Asn Ala Pro Ser Leu Val Ala Ile Gly Arg Arg Ser Glu Ser
        275                 280                 285 gac tgc ttg tct gag gag ctt cgc cac atg gat cca gat ttg ggc tac    912
Asp Cys Leu Ser Glu Glu Leu Arg His Met Asp Pro Asp Leu Gly Tyr
    290                 295                 300 cag cac gca cta tcc ggc ttg tcc agc gtc aag ctg gaa acc gtc taa    960
Gln His Ala Leu Ser Gly Leu Ser Ser Val Lys Leu Glu Thr Val
305                 310                 315

<210> SEQ ID NO 8
<211> LENGTH: 319
<212> TYPE: PRT
<213> ORGANISM: Corynebacterium glutamicum

<400> SEQUENCE: 8

Met Ile Phe Glu Leu Pro Asp Thr Thr Gln Gln Ile Ser Lys Thr
1               5                   10                  15

Leu Thr Arg Leu Arg Glu Ser Gly Thr Gln Val Thr Thr Gly Arg Val
            20                  25                  30

Leu Thr Leu Ile Val Val Thr Asp Ser Glu Ser Asp Val Ala Ala Val
        35                  40                  45

Thr Glu Ser Thr Asn Glu Ala Ser Arg Glu His Pro Ser Arg Val Ile
    50                  55                  60

Ile Leu Val Val Gly Asp Lys Thr Ala Glu Asn Lys Val Asp Ala Glu
65                  70                  75                  80

Val Arg Ile Gly Gly Asp Ala Gly Ala Ser Glu Met Ile Ile Met His
                85                  90                  95

Leu Asn Gly Pro Val Ala Asp Lys Leu Gln His Val Val Thr Pro Leu
            100                 105                 110

Leu Leu Pro Asp Thr Pro Ile Val Ala Trp Trp Pro Gly Glu Ser Pro
        115                 120                 125

Lys Asn Pro Ser Gln Asp Pro Ile Gly Arg Ile Ala Gln Arg Arg Ile
    130                 135                 140

Thr Asp Ala Leu Tyr Asp Arg Asp Ala Leu Glu Asp Arg Val Glu
145                 150                 155                 160

Asn Tyr His Pro Gly Asp Thr Asp Met Thr Trp Ala Arg Leu Thr Gln
                165                 170                 175
```

```
Trp Arg Gly Leu Val Ala Ser Ser Leu Asp His Pro His Ser Glu
            180                 185                 190
Ile Thr Ser Val Arg Leu Thr Gly Ala Ser Gly Ser Thr Ser Val Asp
        195                 200                 205
Leu Ala Ala Gly Trp Leu Ala Arg Arg Leu Asn Val Pro Val Ile Arg
210                 215                 220
Glu Val Thr Asp Ala Pro Thr Val Ser Thr Asp Glu Phe Gly Thr Pro
225                 230                 235                 240
Leu Leu Ala Ile Gln Arg Leu Glu Ile Val Arg Thr Thr Gly Ser Ile
            245                 250                 255
Ile Ile Thr Ile His Asp Ala His Thr Leu Gln Val Glu Met Pro Glu
            260                 265                 270
Ser Gly Asn Ala Pro Ser Leu Val Ala Ile Gly Arg Arg Ser Glu Ser
            275                 280                 285
Asp Cys Leu Ser Glu Glu Leu Arg His Met Asp Pro Asp Leu Gly Tyr
    290                 295                 300
Gln His Ala Leu Ser Gly Leu Ser Ser Val Lys Leu Glu Thr Val
305                 310                 315

<210> SEQ ID NO 9
<211> LENGTH: 1600
<212> TYPE: DNA
<213> ORGANISM: Corynebacterium glutamicum
<220> FEATURE:
<221> NAME/KEY: CDS
<222> LOCATION: (335)..(1291)
<223> OTHER INFORMATION: opcA allele
<220> FEATURE:
<221> NAME/KEY: mutation
<222> LOCATION: (653)..(653)
<223> OTHER INFORMATION: T -> C transition
<220> FEATURE:
<221> NAME/KEY: mutation
<222> LOCATION: (736)..(736)
<223> OTHER INFORMATION: C -> T transition
<220> FEATURE:
<221> NAME/KEY: mutation
<222> LOCATION: (934)..(934)
<223> OTHER INFORMATION: T -> C transition
<220> FEATURE:
<221> NAME/KEY: mutation
<222> LOCATION: (982)..(982)
<223> OTHER INFORMATION: G -> C transversion
<220> FEATURE:
<221> NAME/KEY: mutation
<222> LOCATION: (991)..(991)
<223> OTHER INFORMATION: A -> C transversion
<220> FEATURE:
<221> NAME/KEY: mutation
<222> LOCATION: (1031)..(1031)
<223> OTHER INFORMATION: C -> T transition
<220> FEATURE:
<221> NAME/KEY: mutation
<222> LOCATION: (1115)..(1115)
<223> OTHER INFORMATION: T -> C transition

<400> SEQUENCE: 9
gtgtgctcat ccgcttcggt tccaaggttc caggttctgc catggaagtc cgtgacgtca     60
acatggactt ctcctactca gaatccttca ctgaagaatc acctgaagca tacgagcgcc    120
tcattttgga tgcgctgtta gatgaatcca gcctcttccc taccaacgag gaagtggaac    180
tgagctggaa gattctggat ccaattcttg aagcatggga tgccgatgga gaaccagagg    240
attacccagc gggtacgtgg ggtccaaaga gcgctgatga aatgctttcc cgcaacggtc    300
acacctggcg caggccataa tttaggggca aaaa atg atc ttt gaa ctt ccg gat    355
                                    Met Ile Phe Glu Leu Pro Asp
                                      1               5
```

```
acc acc acc cag caa att tcc aag acc cta act cga ctg cgt gaa tcg    403
Thr Thr Thr Gln Gln Ile Ser Lys Thr Leu Thr Arg Leu Arg Glu Ser
         10                  15                  20 ggc acc cag gtc acc acc ggc cga gtg ctc acc ctc atc gtg gtc act    451
Gly Thr Gln Val Thr Thr Gly Arg Val Leu Thr Leu Ile Val Val Thr
     25                  30                  35 gac tcc gaa agc gat gtc gct gca gtt acc gag tcc acc aat gaa gcc    499
Asp Ser Glu Ser Asp Val Ala Ala Val Thr Glu Ser Thr Asn Glu Ala
40              45                  50                  55 tcg cgc gag cac cca tct cgc gtg atc att ttg gtg gtt ggc gat aaa    547
Ser Arg Glu His Pro Ser Arg Val Ile Ile Leu Val Val Gly Asp Lys
                 60                  65                  70 act gca gaa aac aaa gtt gac gca gaa gtc cgt atc ggt ggc gac gct    595
Thr Ala Glu Asn Lys Val Asp Ala Glu Val Arg Ile Gly Gly Asp Ala
             75                  80                  85 ggt gct tcc gag atg atc atc atg cat ctc aac gga cct gtc gct gac    643
Gly Ala Ser Glu Met Ile Ile Met His Leu Asn Gly Pro Val Ala Asp
         90                  95                 100 aag ctc cag cat gtc gtc aca cca ctg ttg ctt cct gac acc ccc atc    691
Lys Leu Gln His Val Val Thr Pro Leu Leu Leu Pro Asp Thr Pro Ile
     105                 110                 115 gtt gct tgg tgg cca ggt gaa tca cca aag aat cct tcc cag gat cca    739
Val Ala Trp Trp Pro Gly Glu Ser Pro Lys Asn Pro Ser Gln Asp Pro
120                 125                 130                 135 att gga cgc atc gca caa cga cgc atc act gat gct ttg tac gac cgt    787
Ile Gly Arg Ile Ala Gln Arg Arg Ile Thr Asp Ala Leu Tyr Asp Arg
                 140                 145                 150 gat gac gca cta gaa gat cgt gtt gag aac tat cac cca ggt gat acc    835
Asp Asp Ala Leu Glu Asp Arg Val Glu Asn Tyr His Pro Gly Asp Thr
             155                 160                 165 gac atg acg tgg gcg cgc ctt acc cag tgg cgg gga ctt gtt gcc tcc    883
Asp Met Thr Trp Ala Arg Leu Thr Gln Trp Arg Gly Leu Val Ala Ser
         170                 175                 180 tca ttg gat cac cca cca cac agc gaa atc act tcc gtg agg ctg acc    931
Ser Leu Asp His Pro Pro His Ser Glu Ile Thr Ser Val Arg Leu Thr
185                 190                 195 ggc gca agc ggc agt acc tcg gtg gat ttg gct gca ggc tgg ttg gcg    979
Gly Ala Ser Gly Ser Thr Ser Val Asp Leu Ala Ala Gly Trp Leu Ala
200                 205                 210                 215 cgc agg ctg aac gtg cct gtg atc cgc gag gtg aca gat gct ccc acc   1027
Arg Arg Leu Asn Val Pro Val Ile Arg Glu Val Thr Asp Ala Pro Thr
                 220                 225                 230 gtg tca acc gat gag ttt ggt act cca ctg ctg gct atc cag cgc ctg   1075
Val Ser Thr Asp Glu Phe Gly Thr Pro Leu Leu Ala Ile Gln Arg Leu
             235                 240                 245 gag atc gtt cgc acc acc ggc tcg atc atc atc acc atc cat gac gct   1123
Glu Ile Val Arg Thr Thr Gly Ser Ile Ile Ile Thr Ile His Asp Ala
         250                 255                 260 cat acc ctt cag gta gag atg ccg gaa tcc ggc aat gcc cca tcg ctg   1171
His Thr Leu Gln Val Glu Met Pro Glu Ser Gly Asn Ala Pro Ser Leu
     265                 270                 275 gtg gct att ggt cgt cga agt gag tcc gac tgc ttg tct gag gag ctt   1219
Val Ala Ile Gly Arg Arg Ser Glu Ser Asp Cys Leu Ser Glu Glu Leu
280                 285                 290                 295 cgc cac atg gat cca gat ttg ggc tac cag cac gca cta tcc ggc ttg   1267
Arg His Met Asp Pro Asp Leu Gly Tyr Gln His Ala Leu Ser Gly Leu
                 300                 305                 310 tcc agc gtc aag ctg gaa acc gtc taaggagaaa tacaacacta tggttgatgt   1321
Ser Ser Val Lys Leu Glu Thr Val
             315
```

-continued

```
agtacgcgca cgcgatactg aagatttggt tgcacaggct gcctccaaat tcattgaggt    1381
tgttgaagca gcaactgcca ataatggcac cgcacaggta gtgctcaccg gtggtggcgc    1441
cggcatcaag ttgctggaaa agctcagcgt tgatgcggct gaccttgcct gggatcgcat    1501
tcatgtgttc ttcggcgatg agcgcaatgt ccctgtcagt gattctgagt ccaatgaggg    1561
ccaggctcgt gaggcactgt tgtccaaggt ttctatccc                          1600
```

<210> SEQ ID NO 10
<211> LENGTH: 319
<212> TYPE: PRT
<213> ORGANISM: Corynebacterium glutamicum

<400> SEQUENCE: 10

```
Met Ile Phe Glu Leu Pro Asp Thr Thr Thr Gln Gln Ile Ser Lys Thr
1               5                   10                  15

Leu Thr Arg Leu Arg Glu Ser Gly Thr Gln Val Thr Thr Gly Arg Val
            20                  25                  30

Leu Thr Leu Ile Val Val Thr Asp Ser Glu Ser Asp Val Ala Ala Val
        35                  40                  45

Thr Glu Ser Thr Asn Glu Ala Ser Arg Glu His Pro Ser Arg Val Ile
    50                  55                  60

Ile Leu Val Val Gly Asp Lys Thr Ala Glu Asn Lys Val Asp Ala Glu
65                  70                  75                  80

Val Arg Ile Gly Gly Asp Ala Gly Ala Ser Glu Met Ile Ile Met His
                85                  90                  95

Leu Asn Gly Pro Val Ala Asp Lys Leu Gln His Val Val Thr Pro Leu
            100                 105                 110

Leu Leu Pro Asp Thr Pro Ile Val Ala Trp Trp Pro Gly Glu Ser Pro
        115                 120                 125

Lys Asn Pro Ser Gln Asp Pro Ile Gly Arg Ile Ala Gln Arg Arg Ile
    130                 135                 140

Thr Asp Ala Leu Tyr Asp Arg Asp Ala Leu Glu Asp Arg Val Glu
145                 150                 155                 160

Asn Tyr His Pro Gly Asp Thr Asp Met Thr Trp Ala Arg Leu Thr Gln
                165                 170                 175

Trp Arg Gly Leu Val Ala Ser Ser Leu Asp His Pro His Ser Glu
            180                 185                 190

Ile Thr Ser Val Arg Leu Thr Gly Ala Ser Gly Ser Thr Ser Val Asp
        195                 200                 205

Leu Ala Ala Gly Trp Leu Ala Arg Arg Leu Asn Val Pro Val Ile Arg
    210                 215                 220

Glu Val Thr Asp Ala Pro Thr Val Ser Thr Asp Glu Phe Gly Thr Pro
225                 230                 235                 240

Leu Leu Ala Ile Gln Arg Leu Glu Ile Val Arg Thr Thr Gly Ser Ile
                245                 250                 255

Ile Ile Thr Ile His Asp Ala His Thr Leu Gln Val Glu Met Pro Glu
            260                 265                 270

Ser Gly Asn Ala Pro Ser Leu Val Ala Ile Gly Arg Arg Ser Glu Ser
        275                 280                 285

Asp Cys Leu Ser Glu Glu Leu Arg His Met Asp Pro Asp Leu Gly Tyr
    290                 295                 300

Gln His Ala Leu Ser Gly Leu Ser Ser Val Lys Leu Glu Thr Val
305                 310                 315
```

```
<210> SEQ ID NO 11
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer opcA-A1

<400> SEQUENCE: 11
cacctggcgc aggccataat                                               20

<210> SEQ ID NO 12
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer opcA-E1

<400> SEQUENCE: 12
cgcgtgcgcg tactacatca                                               20

<210> SEQ ID NO 13
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer opcA-int1

<400> SEQUENCE: 13
acggacctgt cgctgacaag                                               20

<210> SEQ ID NO 14
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer opcA-int2

<400> SEQUENCE: 14
cggattccgg catctctacc                                               20

<210> SEQ ID NO 15
<211> LENGTH: 519
<212> TYPE: DNA
<213> ORGANISM: Corynebacterium glutamicum
<220> FEATURE:
<221> NAME/KEY: CDS
<222> LOCATION: (1)..(519)
<223> OTHER INFORMATION: reading frame
<220> FEATURE:
<221> NAME/KEY: mutation
<222> LOCATION: (28)..(28)
<223> OTHER INFORMATION: C in position 28 corresponds to C in position
      319 of SEQ ID NO: 5
<220> FEATURE:
<221> NAME/KEY: mutation
<222> LOCATION: (366)..(366)
<223> OTHER INFORMATION: C in position 366 corresponds to C in position
      657 of SEQ ID NO: 5
<220> FEATURE:
<221> NAME/KEY: mutation
<222> LOCATION: (406)..(406)
<223> OTHER INFORMATION: T in position 406 corresponds to T in position
      697 in SEQ ID NO: 5
```

```
<220> FEATURE:
<221> NAME/KEY: mutation
<222> LOCATION: (490)..(490)
<223> OTHER INFORMATION: C in position 490 corresponds to C in position
      781 in SEQ ID NO: 5

<400> SEQUENCE: 15 aac gga cct gtc gct gac aag ctc cag cat gtc gtc aca cca ctg ttg      48
Asn Gly Pro Val Ala Asp Lys Leu Gln His Val Val Thr Pro Leu Leu
1               5                   10                  15 ctt cct gac acc ccc atc gtt gct tgg tgg cca ggt gaa tca cca aag      96
Leu Pro Asp Thr Pro Ile Val Ala Trp Trp Pro Gly Glu Ser Pro Lys
            20                  25                  30 aat cct tcc cag gac cca att gga cgc atc gca caa cga cgc atc act     144
Asn Pro Ser Gln Asp Pro Ile Gly Arg Ile Ala Gln Arg Arg Ile Thr
        35                  40                  45 gat gct ttg tac gac cgt gat gac gca cta gaa gat cgt gtt gag aac     192
Asp Ala Leu Tyr Asp Arg Asp Asp Ala Leu Glu Asp Arg Val Glu Asn
50                  55                  60 tat cac cca ggt gat acc gac atg acg tgg gcg cgc ctt acc cag tgg     240
Tyr His Pro Gly Asp Thr Asp Met Thr Trp Ala Arg Leu Thr Gln Trp
65                  70                  75                  80 cgg gga ctt gtt gcc tcc tca ttg gat cac cca cca cac agc gaa atc     288
Arg Gly Leu Val Ala Ser Ser Leu Asp His Pro Pro His Ser Glu Ile
                85                  90                  95 act tcc gtg agg ctg acc ggt gca agc ggc agt acc tcg gtg gat ttg     336
Thr Ser Val Arg Leu Thr Gly Ala Ser Gly Ser Thr Ser Val Asp Leu
            100                 105                 110 gct gca ggc tgg ttg gcg cgg agg ctg aac gtg cct gtg atc cgc gag     384
Ala Ala Gly Trp Leu Ala Arg Arg Leu Asn Val Pro Val Ile Arg Glu
        115                 120                 125 gtg aca gat gct ccc acc gtg tca acc gat gag ttt ggt act cca ctg     432
Val Thr Asp Ala Pro Thr Val Ser Thr Asp Glu Phe Gly Thr Pro Leu
130                 135                 140 ctg gct atc cag cgc ctg gag atc gtt cgc acc acc ggc tcg atc atc     480
Leu Ala Ile Gln Arg Leu Glu Ile Val Arg Thr Thr Gly Ser Ile Ile
145                 150                 155                 160 atc acc atc cat gac gct cat acc ctt cag gta gag atg                  519
Ile Thr Ile His Asp Ala His Thr Leu Gln Val Glu Met
                165                 170

<210> SEQ ID NO 16
<211> LENGTH: 173
<212> TYPE: PRT
<213> ORGANISM: Corynebacterium glutamicum

<400> SEQUENCE: 16

Asn Gly Pro Val Ala Asp Lys Leu Gln His Val Val Thr Pro Leu Leu
1               5                   10                  15

Leu Pro Asp Thr Pro Ile Val Ala Trp Trp Pro Gly Glu Ser Pro Lys
            20                  25                  30

Asn Pro Ser Gln Asp Pro Ile Gly Arg Ile Ala Gln Arg Arg Ile Thr
        35                  40                  45

Asp Ala Leu Tyr Asp Arg Asp Asp Ala Leu Glu Asp Arg Val Glu Asn
50                  55                  60

Tyr His Pro Gly Asp Thr Asp Met Thr Trp Ala Arg Leu Thr Gln Trp
65                  70                  75                  80

Arg Gly Leu Val Ala Ser Ser Leu Asp His Pro Pro His Ser Glu Ile
                85                  90                  95

Thr Ser Val Arg Leu Thr Gly Ala Ser Gly Ser Thr Ser Val Asp Leu
            100                 105                 110
```

```
Ala Ala Gly Trp Leu Ala Arg Arg Leu Asn Val Pro Val Ile Arg Glu
            115                 120                 125

Val Thr Asp Ala Pro Thr Val Ser Thr Asp Glu Phe Gly Thr Pro Leu
        130                 135                 140

Leu Ala Ile Gln Arg Leu Glu Ile Val Arg Thr Thr Gly Ser Ile Ile
145                 150                 155                 160

Ile Thr Ile His Asp Ala His Thr Leu Gln Val Glu Met
                165                 170

<210> SEQ ID NO 17
<211> LENGTH: 519
<212> TYPE: DNA
<213> ORGANISM: Corynebacterium glutamicum
<220> FEATURE:
<221> NAME/KEY: CDS
<222> LOCATION: (1)..(519)
<223> OTHER INFORMATION: reading frame
<220> FEATURE:
<221> NAME/KEY: mutation
<222> LOCATION: (28)..(28)
<223> OTHER INFORMATION: C in position 28 corresponds to C in position
      319 of SEQ ID NO: 7
<220> FEATURE:
<221> NAME/KEY: mutation
<222> LOCATION: (111)..(111)
<223> OTHER INFORMATION: T in position 111 corresponds to T in position
      402 in SEQ ID NO: 7.
<220> FEATURE:
<221> NAME/KEY: mutation
<222> LOCATION: (309)..(309)
<223> OTHER INFORMATION: C in position 309 corresponds to C in position
      600 in SEQ ID NO: 7
<220> FEATURE:
<221> NAME/KEY: mutation
<222> LOCATION: (357)..(357)
<223> OTHER INFORMATION: C in position 357 corresponds to C in position
      648 of SEQ ID NO: 7
<220> FEATURE:
<221> NAME/KEY: mutation
<222> LOCATION: (366)..(366)
<223> OTHER INFORMATION: C in position 366 corresponds to C in position
      657 in SEQ ID NO: 7
<220> FEATURE:
<221> NAME/KEY: mutation
<222> LOCATION: (406)..(406)
<223> OTHER INFORMATION: T in position 406 corresponds to T in position
      697 in SEQ ID NO:7
<220> FEATURE:
<221> NAME/KEY: mutation
<222> LOCATION: (490)..(490)
<223> OTHER INFORMATION: C in position 490 corresponds to C in position
      781 of SEQ ID NO: 7

<400> SEQUENCE: 17 aac gga cct gtc gct gac aag ctc cag cat gtc gtc aca cca ctg ttg      48
Asn Gly Pro Val Ala Asp Lys Leu Gln His Val Val Thr Pro Leu Leu
1               5                   10                  15 ctt cct gac acc ccc atc gtt gct tgg tgg cca ggt gaa tca cca aag      96
Leu Pro Asp Thr Pro Ile Val Ala Trp Trp Pro Gly Glu Ser Pro Lys
            20                  25                  30 aat cct tcc cag gat cca att gga cgc atc gca caa cga cgc atc act     144
Asn Pro Ser Gln Asp Pro Ile Gly Arg Ile Ala Gln Arg Arg Ile Thr
        35                  40                  45 gat gct ttg tac gac cgt gat gac gca cta gaa gat cgt gtt gag aac     192
Asp Ala Leu Tyr Asp Arg Asp Asp Ala Leu Glu Asp Arg Val Glu Asn
    50                  55                  60 tat cac cca ggt gat acc gac atg acg tgg gcg cgc ctt acc cag tgg     240
Tyr His Pro Gly Asp Thr Asp Met Thr Trp Ala Arg Leu Thr Gln Trp
65                  70                  75                  80
```

```
cgg gga ctt gtt gcc tcc tca ttg gat cac cca cca cac agc gaa atc    288
Arg Gly Leu Val Ala Ser Ser Leu Asp His Pro Pro His Ser Glu Ile
            85                  90                  95 act tcc gtg agg ctg acc ggc gca agc ggc agt acc tcg gtg gat ttg    336
Thr Ser Val Arg Leu Thr Gly Ala Ser Gly Ser Thr Ser Val Asp Leu
        100                 105                 110 gct gca ggc tgg ttg gcg cgc agg ctg aac gtg cct gtg atc cgc gag    384
Ala Ala Gly Trp Leu Ala Arg Arg Leu Asn Val Pro Val Ile Arg Glu
    115                 120                 125 gtg aca gat gct ccc acc gtg tca acc gat gag ttt ggt act cca ctg    432
Val Thr Asp Ala Pro Thr Val Ser Thr Asp Glu Phe Gly Thr Pro Leu
130                 135                 140 ctg gct atc cag cgc ctg gag atc gtt cgc acc acc ggc tcg atc atc    480
Leu Ala Ile Gln Arg Leu Glu Ile Val Arg Thr Thr Gly Ser Ile Ile
145                 150                 155                 160 atc acc atc cat gac gct cat acc ctt cag gta gag atg                 519
Ile Thr Ile His Asp Ala His Thr Leu Gln Val Glu Met
                165                 170

<210> SEQ ID NO 18
<211> LENGTH: 173
<212> TYPE: PRT
<213> ORGANISM: Corynebacterium glutamicum

<400> SEQUENCE: 18

Asn Gly Pro Val Ala Asp Lys Leu Gln His Val Thr Pro Leu Leu
1               5                   10                  15

Leu Pro Asp Thr Pro Ile Val Ala Trp Trp Pro Gly Glu Ser Pro Lys
            20                  25                  30

Asn Pro Ser Gln Asp Pro Ile Gly Arg Ile Ala Gln Arg Arg Ile Thr
        35                  40                  45

Asp Ala Leu Tyr Asp Arg Asp Ala Leu Glu Asp Arg Val Glu Asn
    50                  55                  60

Tyr His Pro Gly Asp Thr Asp Met Thr Trp Ala Arg Leu Thr Gln Trp
65                  70                  75                  80

Arg Gly Leu Val Ala Ser Ser Leu Asp His Pro Pro His Ser Glu Ile
            85                  90                  95

Thr Ser Val Arg Leu Thr Gly Ala Ser Gly Ser Thr Ser Val Asp Leu
        100                 105                 110

Ala Ala Gly Trp Leu Ala Arg Arg Leu Asn Val Pro Val Ile Arg Glu
    115                 120                 125

Val Thr Asp Ala Pro Thr Val Ser Thr Asp Glu Phe Gly Thr Pro Leu
130                 135                 140

Leu Ala Ile Gln Arg Leu Glu Ile Val Arg Thr Thr Gly Ser Ile Ile
145                 150                 155                 160

Ile Thr Ile His Asp Ala His Thr Leu Gln Val Glu Met
                165                 170

<210> SEQ ID NO 19
<211> LENGTH: 1263
<212> TYPE: DNA
<213> ORGANISM: Corynebacterium glutamicum
<220> FEATURE:
<221> NAME/KEY: CDS
<222> LOCATION: (1)..(1263)
<223> OTHER INFORMATION: lysC wild type gene

<400> SEQUENCE: 19 gtg gcc ctg gtc gta cag aaa tat ggc ggt tcc tcg ctt gag agt gcg    48
Met Ala Leu Val Val Gln Lys Tyr Gly Gly Ser Ser Leu Glu Ser Ala
1               5                   10                  15
```

```
gaa cgc att aga aac gtc gct gaa cgg atc gtt gcc acc aag aag gct    96
Glu Arg Ile Arg Asn Val Ala Glu Arg Ile Val Ala Thr Lys Lys Ala
         20                  25                  30 gga aat gat gtc gtg gtt gtc tgc tcc gca atg gga gac acc acg gat   144
Gly Asn Asp Val Val Val Val Cys Ser Ala Met Gly Asp Thr Thr Asp
         35                  40                  45 gaa ctt cta gaa ctt gca gcg gca gtg aat ccc gtt ccg cca gct cgt   192
Glu Leu Leu Glu Leu Ala Ala Ala Val Asn Pro Val Pro Pro Ala Arg
 50                  55                  60 gaa atg gat atg ctc ctg act gct ggt gag cgt att tct aac gct ctc   240
Glu Met Asp Met Leu Leu Thr Ala Gly Glu Arg Ile Ser Asn Ala Leu
 65                  70                  75                  80 gtc gcc atg gct att gag tcc ctt ggc gca gaa gcc caa tct ttc acg   288
Val Ala Met Ala Ile Glu Ser Leu Gly Ala Glu Ala Gln Ser Phe Thr
                     85                  90                  95 ggc tct cag gct ggt gtg ctc acc acc gag cgc cac gga aac gca cgc   336
Gly Ser Gln Ala Gly Val Leu Thr Thr Glu Arg His Gly Asn Ala Arg
            100                 105                 110 att gtt gat gtc act cca ggt cgt gtg cgt gaa gca ctc gat gag ggc   384
Ile Val Asp Val Thr Pro Gly Arg Val Arg Glu Ala Leu Asp Glu Gly
        115                 120                 125 aag atc tgc att gtt gct ggt ttc cag ggt gtt aat aaa gaa acc cgc   432
Lys Ile Cys Ile Val Ala Gly Phe Gln Gly Val Asn Lys Glu Thr Arg
    130                 135                 140 gat gtc acc acg ttg ggt cgt ggt ggt tct gac acc act gca gtt gcg   480
Asp Val Thr Thr Leu Gly Arg Gly Gly Ser Asp Thr Thr Ala Val Ala
145                 150                 155                 160 ttg gca gct gct ttg aac gct gat gtg tgt gag att tac tcg gac gtt   528
Leu Ala Ala Ala Leu Asn Ala Asp Val Cys Glu Ile Tyr Ser Asp Val
                    165                 170                 175 gac ggt gtg tat acc gct gac ccg cgc atc gtt cct aat gca cag aag   576
Asp Gly Val Tyr Thr Ala Asp Pro Arg Ile Val Pro Asn Ala Gln Lys
                180                 185                 190 ctg gaa aag ctc agc ttc gaa gaa atg ctg gaa ctt gct gct gtt ggc   624
Leu Glu Lys Leu Ser Phe Glu Glu Met Leu Glu Leu Ala Ala Val Gly
            195                 200                 205 tcc aag att ttg gtg ctg cgc agt gtt gaa tac gct cgt gca ttc aat   672
Ser Lys Ile Leu Val Leu Arg Ser Val Glu Tyr Ala Arg Ala Phe Asn
        210                 215                 220 gtg cca ctt cgc gta cgc tcg tct tat agt aat gat ccc ggc act ttg   720
Val Pro Leu Arg Val Arg Ser Ser Tyr Ser Asn Asp Pro Gly Thr Leu
225                 230                 235                 240 att gcc ggc tct atg gag gat att cct gtg gaa gaa gca gtc ctt acc   768
Ile Ala Gly Ser Met Glu Asp Ile Pro Val Glu Glu Ala Val Leu Thr
                245                 250                 255 ggt gtc gca acc gac aag tcc gaa gcc aaa gta acc gtt ctg ggt att   816
Gly Val Ala Thr Asp Lys Ser Glu Ala Lys Val Thr Val Leu Gly Ile
                260                 265                 270 tcc gat aag cca ggc gag gct gcg aag gtt ttc cgt gcg ttg gct gat   864
Ser Asp Lys Pro Gly Glu Ala Ala Lys Val Phe Arg Ala Leu Ala Asp
            275                 280                 285 gca gaa atc aac att gac atg gtt ctg cag aac gtc tct tct gta gaa   912
Ala Glu Ile Asn Ile Asp Met Val Leu Gln Asn Val Ser Ser Val Glu
        290                 295                 300 gac ggc acc acc gac atc acc ttc acc tgc cct cgt tcc gac ggc cgc   960
Asp Gly Thr Thr Asp Ile Thr Phe Thr Cys Pro Arg Ser Asp Gly Arg
305                 310                 315                 320 cgc gcg atg gag atc ttg aag aag ctt cag gtt cag ggc aac tgg acc  1008
Arg Ala Met Glu Ile Leu Lys Lys Leu Gln Val Gln Gly Asn Trp Thr
                325                 330                 335
```

```
aat gtg ctt tac gac gac cag gtc ggc aaa gtc tcc ctc gtg ggt gct    1056
Asn Val Leu Tyr Asp Asp Gln Val Gly Lys Val Ser Leu Val Gly Ala
        340                 345                 350 ggc atg aag tct cac cca ggt gtt acc gca gag ttc atg gaa gct ctg    1104
Gly Met Lys Ser His Pro Gly Val Thr Ala Glu Phe Met Glu Ala Leu
            355                 360                 365 cgc gat gtc aac gtg aac atc gaa ttg att tcc acc tct gag att cgt    1152
Arg Asp Val Asn Val Asn Ile Glu Leu Ile Ser Thr Ser Glu Ile Arg
    370                 375                 380 att tcc gtg ctg atc cgt gaa gat gat ctg gat gct gct gca cgt gca    1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat    1248
Leu His Glu Gln Phe Gln Leu Gly Gly Glu Asp Glu Ala Val Val Tyr
                405                 410                 415 gca ggc acc gga cgc                                                 1263
Ala Gly Thr Gly Arg
            420

<210> SEQ ID NO 20
<211> LENGTH: 421
<212> TYPE: PRT
<213> ORGANISM: Corynebacterium glutamicum

<400> SEQUENCE: 20

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255
```

-continued

| | | | | | | | | | | | | | |
|---|---|---|---|---|---|---|---|---|---|---|---|---|---|
|Gly|Val|Ala|Thr|Asp|Lys|Ser|Glu|Ala|Lys|Val|Thr|Val|Leu Gly Ile|
| | | |260| | | |265| | | |270| | |
|Ser|Asp|Lys|Pro|Gly|Glu|Ala|Ala|Lys|Val|Phe|Arg|Ala|Leu Ala Asp|
| | |275| | | |280| | | |285| | | |
|Ala|Glu|Ile|Asn|Ile|Asp|Met|Val|Leu|Gln|Asn|Val|Ser|Ser Val Glu|
| |290| | | |295| | | |300| | | | |
|Asp Gly|Thr|Thr|Asp|Ile|Thr|Phe|Thr|Cys|Pro|Arg|Ser|Asp|Gly Arg|
|305| | |310| | | |315| | | | |320| |
|Arg Ala|Met|Glu|Ile|Leu|Lys|Lys|Leu|Gln|Val|Gln|Gly|Asn|Trp Thr|
| | | |325| | | |330| | | |335| | |
|Asn Val|Leu|Tyr|Asp|Asp|Gln|Val|Gly|Lys|Val|Ser|Leu|Val Gly Ala|
| | |340| | | |345| | | |350| | | |
|Gly Met|Lys|Ser|His|Pro|Gly|Val|Thr|Ala|Glu|Phe|Met|Glu Ala Leu|
| |355| | | |360| | | |365| | | | |
|Arg Asp|Val|Asn|Val|Asn|Ile|Glu|Leu|Ile|Ser|Thr|Ser|Glu|Ile Arg|
|370| | |375| | | |380| | | | | | |
|Ile Ser|Val|Leu|Ile|Arg|Glu|Asp|Asp|Leu|Asp|Ala|Ala|Ala Arg Ala|
|385| | |390| | | |395| | | | |400| |
|Leu His|Glu|Gln|Phe|Gln|Leu|Gly|Gly|Glu|Asp|Glu|Ala|Val Val Tyr|
| | |405| | | |410| | | |415| | | |
|Ala Gly|Thr|Gly|Arg| | | | | | | | | | |